United States Patent
Vrana et al.

(10) Patent No.: US 8,647,825 B2
(45) Date of Patent: Feb. 11, 2014

(54) COMPOSITIONS AND METHODS RELATING TO MONITORING ALCOHOL CONSUMPTION AND ALCOHOL ABUSE

(75) Inventors: Kent E. Vrana, Hummelstown, PA (US); Willard M. Freeman, Hershey, PA (US); Kathleen A. Grant, Portland, OR (US); Steve Gonzales, Beaverton, OR (US)

(73) Assignee: The Penn State Research Foundation, University Park, PA (US)

( * ) Notice: Subject to any disclaimer, the term of this patent is extended or adjusted under 35 U.S.C. 154(b) by 124 days.

(21) Appl. No.: 12/987,425

(22) Filed: Jan. 10, 2011

(65) Prior Publication Data

US 2011/0212847 A1 Sep. 1, 2011

Related U.S. Application Data

(60) Provisional application No. 61/293,358, filed on Jan. 8, 2010.

(51) Int. Cl.
*G01N 33/53* (2006.01)
*A61K 49/00* (2006.01)

(52) U.S. Cl.
USPC .................................... 435/7.1; 424/9.1

(58) Field of Classification Search
None
See application file for complete search history.

(56) References Cited

U.S. PATENT DOCUMENTS

| | | | |
|---|---|---|---|
| 4,463,098 A | 7/1984 | Hoberman | |
| 4,814,280 A | 3/1989 | Peterson | |
| 5,066,583 A | 11/1991 | Mueller | |
| 5,702,904 A | 12/1997 | Makhlouf et al. | |
| 5,747,346 A | 5/1998 | Pullarkat et al. | |
| 5,823,196 A | 10/1998 | Harasymiw | |
| 5,958,785 A | 9/1999 | Pullarkat et al. | |
| 6,498,038 B1 | 12/2002 | Ghosh et al. | |
| 6,814,951 B1 | 11/2004 | Thiele et al. | |
| 7,314,720 B2 | 1/2008 | De La Paz et al. | |
| 2003/0104457 A1 | 6/2003 | Harris et al. | |
| 2006/0084057 A1 | 4/2006 | Rose et al. | |
| 2006/0135420 A1 | 6/2006 | Mato De La Paz et al. | |
| 2006/0172286 A1 | 8/2006 | Poynard | |
| 2008/0145864 A1 | 6/2008 | Poynard | |
| 2011/0065599 A1* | 3/2011 | LaBrie et al. ..................... 506/9 |

FOREIGN PATENT DOCUMENTS

WO WO-2008/095136 8/2008

OTHER PUBLICATIONS

Hack Integrated transcriptome and proteome data: the challenges ahead; Briefings in functional genomics and proteomics, vol. 3, No. 3, 212-219, 2004.*

Rossi et al., Assessing liver fibrosis with serum marker models; Clin Biochem Rev, vol. 28, pp. 3-10, 2007.*
Ponomarenko et al., Effects of alcohol consumption on eight circulating markers of liver fibrosis; Alcohol and Alcoholism, vol. 37, No. 3, pp. 252-255, 2002.*
Buechler et al., Elevated adiponectin serum levels in patients with chronic alcohol abuse rapidly decline during alcohol withdrawal; Hepatology, vol. 24, pp. 558-543, 2008.*
Collins et al., the application of genomic and proteomic technologies in predictive, preventive and personalized medicine; Vascular Pharmacology, vol. 45, pp. 258-267, 2006.*
Leksowski et al, Immunological parameters in patients suffering from alcohol-dependence syndrome; Immunopharmacology, vol. 46, pp. 65-70, 2000.*
Gonzalez-Quintela et al., Association of alcohol consumption with total seum immunoglobulin E levels and allergic sensitization in an adult population-based survey; Clin Exp Allergy, vol. 33, pp. 199-205, 2003.*
Cheung et al., The HCV serum proteome: a search for fibrosis protein markers; J of Viral Hepatitis, vol. 16, pp. 418-429, 2009.*
Ponnappa et al., Modeling alcohol's effects on organs in animal models; Alcohol Research and Health, vol. 24, No. 2, pp. 93-104, 2000.*
Tavakoli et al., Review of current clinical biomarkers for the detction of alcohol dependence; Innov Clin Neurosci, vol. 8, No. 3, pp. 26-33, 2011.*
Conigrave, K.M. et al., Diagnostic Tests for Alcohol Consumption, *Alcohol Alcohol*, 30(1): 13-26, Jan. 1995 (Abstract only).
Das, S.K. et al., Biomarkers of Alcoholism: An Updated Review, *The Scandinavian Journal of Clinical & Laboratory Investigation*, 68(2): 81-92, Apr. 2008.
Friedrich, N. et al., The Association Between Alcohol Consumption and Biomarkers of Alcohol Exposure with Total Serum Immunoglobulin E Levels, *Alcohol Clin Exp Res*, Jun. 2008; 32(6):983-90, Epub Apr. 26, 2008 (Abstract only).
Hannukesla, M.L. et al., Biochemical Markers of Alcoholism, *Clin Chem Lab Med*, 45(8):953-61, 2007 (Abstract only).
Musshoff, F. et al., Determination of Biological Markers for Alcohol Abuse, *J Chromatogr B Blamed Sci Appl*, 713(1): 245-64, Aug. 21, 1998 (Abstract only).
Peterson, K., Biomarkers for Alcohol Use and Abuse-A Summary, *Alcohol Res Health*, 28(1):30-7, 2004-2005 (Abstract only).
Ponomarenko, P. et al., Effects of Alcohol Consumption on Eight Circulating Markers of Liver Fibrosis, *Alcohol & Alcoholism*, 37(2):252-55, 2002.
Rosman, A. et al., Diagnostic Utility of Laboratory Tests in Alcoholic Liver Disease, *Clin Chem*, 40(8): 1641-51, 1995.
Sharpe, PC, Biochemical Detection and Monitoring of Alcohol Abuse and Abstinence, *Ann Clin Biochem*, 39(Pt 6): 652-64, Nov. 2001 (Abstract only).
Naveau, S. et al., Alpha-2-macroglobulin and hepatic fibrosis. Diagnostic interest, *Dig Dis Sci*, 39(11): 22426-32, Nov. 1994 (Abstract only).

(Continued)

*Primary Examiner* — Celine Qian
*Assistant Examiner* — Addison D Ault
(74) *Attorney, Agent, or Firm* — Gifford, Krass, Sprinkle, Anderson & Citkowski, P.C.

(57) ABSTRACT

Methods and compositions according to embodiments of the present invention are provided that specifically and sensitively detect alcohol consumption and whether alcohol consumption is moderate or high in a subject. Aspects of the present invention relate to assays of panels of proteins for detecting non-consumption, moderate consumption and high consumption of ethanol by a subject.

12 Claims, 30 Drawing Sheets

(56) References Cited

OTHER PUBLICATIONS

Stefanini, G. et al., In vivo effect of chronic ethanol abuse on membrane alpha 1-glycoprotein of lymphocytes and immune response to various stimulating agents, *Alcohol Clin Exp Res*, 13(3): 444-8, Jun. 1989 (Abstract only).

Joosten, M. et al., Moderate alcohol consumption increases insulin sensitivity and ADIPOQ expression in postmenopausal women: a randomised, crossover trial, *Diabetologia*, 51: 137-581, 2008.

Andrade, M. et al., Short-term Administration of Ethanol in Mice Deviates Antigen Presentation Activity Towards B Cells, *Scandinavian Journal of Immunology*, 70: 226-37, 2009.

Walker, Jr., E. et al., Ethanol Exposure Impairs LPS-Induced Pulmonary LIX Expression: Alveolar Epithelial Cell Dysfunction as a Consequence of Acute Intoxication, *Alcohol Clinical and Experimental Research*, 33(2): 357-65, 2009.

\* cited by examiner

|  | Alcohol Abuse | No Alcohol Abuse |
|---|---|---|
| Training Set | 10 | 20 |
| Test Set | 10 | 20 |
| Classified as Alcohol Abuse | 10 | 4 |
| Classified as No Alcohol Abuse | 0 | 16 |

100% Sens  80% Spec  71% PPV  100% NPV  87% Accuracy

FIGURE 5A

|  | Alcohol Use | No Alcohol Use |
|---|---|---|
| Training Set | 20 | 10 |
| Test Set | 20 | 10 |
| Classified as Alcohol Use | 20 | 1 |
| Classified as No Alcohol Use | 0 | 9 |

100% Sens  90% Spec  97% PPV  95% NPV  97% Accuracy

FIGURE 5B

COMPOSITIONS AND METHODS RELATING TO MONITORING ALCOHOL CONSUMPTION AND ALCOHOL ABUSE

REFERENCE TO RELATED APPLICATION

This application claims priority from U.S. Provisional Application Ser. No. 61/293,358, filed Jan. 8, 2010, the entire content of which is incorporated herein by reference.

GOVERNMENT SUPPORT

This invention was made with government support under Grant Nos. AA016613, AA11997, AA13510 and AA13641 awarded by the U.S. National Institutes of Health. The government has certain rights in the invention.

FIELD OF THE INVENTION

The present invention relates generally to methods and compositions for detecting non-consumption, moderate consumption and high consumption of ethanol by a subject. Embodiments of the present invention relate to detection of a panel of proteins for detecting non-consumption, moderate consumption and high consumption of ethanol by a subject.

BACKGROUND OF THE INVENTION

Alcohol abuse and alcoholism represent a tremendous burden on society. In the United States, the annual economic burden of alcohol abuse and alcoholism is estimated to be 185 billion dollars due to lost productivity, medical, legal and property damage. The current estimate of the number of Americans that meet the diagnostic criteria of alcohol abuse or dependence is 14 million. Abusive alcohol consumption, defined as >6 drinks per day and 20% of daily calories in the form of alcohol, is co-morbid with brain, heart, liver, pancreatic, and kidney disease states. Moreover, alcohol abuse is a cofactor in cancer, reproductive, and immune system dysfunction.

A number of potential markers of alcohol abuse have been studied, including gamma-glutamyltransferase, carbohydrate deficient transferrin, and mean corpuscular volume. These markers lack the specificity and selectivity to positively identify drinkers while simultaneously not falsely identifying non-drinkers as described in Hannuksela et al., Clin Chem Lab Med., 2007, 45(8):953-61.

Thus, there is a continuing need for biomarkers that specifically and sensitively identify non-consumption, moderate consumption and high consumption of ethanol in a subject.

SUMMARY OF THE INVENTION

Methods of detecting and characterizing alcohol consumption in a subject are provided according to aspects of the present invention which include assaying a subject sample for 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 biomarkers selected from: A1BG, A2M, ADIPQ, APCS1, APCS2, APOAI, APOC3, C3, C4a, C9, CALCA, CCL3, CCL4, CD40, CLU, CSF2, CXCL5, EGF, F3, F7, FABP3, FN1, GOT1, HRG, IgE, IGF1, IL12p70, IL18, IL2, IL7, ITIH4, KITLG, KLK3, MMP2, RBP4, SAA4, SERPINF1, THPO, VCAM1 and VEGFA, to determine the level of the biomarkers in the sample. The levels of the two or more biomarkers are compared to a standard to detect an increase or decrease in the level of each biomarker, thereby detecting and characterizing alcohol consumption in the subject. Each biomarker can be assayed in a separate aliquot of the sample. Alternatively, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 of the biomarkers can be assayed together in multiplex format.

Methods of detecting and characterizing alcohol consumption in a subject are provided according to aspects of the present invention which include assaying a subject sample for 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 or 38 biomarkers selected from: A1BG, A2M, ADIPQ, APCS1, APCS2, APOAI, APOC3, C3, C4a, C9, CALCA, CCL3, CCL4, CD40, CLU, CSF2, CXCL5, EGF, F3, F7, FABP3, FN1, GOT1, HRG, IgE, IGF1, IL12p70, IL18, IL2, IL7, KITLG, KLK3, MMP2, SAA4, SERPINF1, THPO, VCAM1 and VEGFA, to determine the level of the biomarkers in the sample. The levels of the assayed biomarkers are compared to a standard to detect an increase or decrease in the level of each assayed biomarker, thereby detecting and characterizing alcohol consumption in the subject. Each biomarker can be assayed in a separate aliquot of the sample. Alternatively, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 or 38 of the biomarkers can be assayed together in multiplex format.

Methods of detecting and characterizing alcohol consumption in a subject are provided according to aspects of the present invention which include assaying a subject sample for 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 biomarkers selected from: A1BG, A2M, ADIPQ, APCS1, APCS2, APOAI, APOC3, C3, C4a, C9, CALCA, CCL3, CCL4, CD40, CLU, CSF2, CXCL5, EGF, F3, F7, FABP3, FN1, GOT1, HRG, IgE, IGF1, IL12p70, IL18, IL2, IL7, ITIH4, KITLG, KLK3, MMP2, RBP4, SAA4, SERPINF1, THPO, VCAM1 and VEGFA, to determine the level of the biomarkers in the sample. The levels of the biomarkers are compared to a standard to detect an increase or decrease in the level of each biomarker, thereby detecting and characterizing alcohol consumption in the subject. Each biomarker can be assayed in a separate aliquot of the sample. Alternatively, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 of the biomarkers can be assayed together in multiplex format Methods of detecting and characterizing alcohol consumption in a subject are provided according to aspects of the present invention which include assaying a subject sample for 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 or 38 biomarkers selected from: A1BG, A2M, ADIPQ, APCS1, APCS2, APOAI, APOC3, C3, C4a, C9, CALCA, CCL3, CCL4, CD40, CLU, CSF2, CXCL5, EGF, F3, F7, FABP3, FN1, GOT1, HRG, IgE, IGF1, IL12p70, IL18, IL2, IL7, KITLG, KLK3, MMP2, SAA4, SERPINF1, THPO, VCAM1 and VEGFA, to determine the level of the biomarkers in the sample. The levels of the assayed biomarkers are compared to a standard to detect an increase or decrease in the level of each assayed biomarker, thereby detecting and characterizing alcohol consumption in the subject. Each biomarker can be assayed in a separate aliquot of the sample. Alternatively, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 or 38 of the biomarkers can be assayed together in multiplex format.

Methods of detecting and characterizing alcohol consumption in a subject are provided according to aspects of the present invention which include assaying a subject sample for 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 biomarkers selected from: A1BG, A2M, ADIPQ, APCS1, APCS2, APOAI, APOC3, C3, C4a, C9, CALCA, CCL3, CCL4, CD40, CLU, CSF2, CXCL5, EGF, F3, F7, FABP3, FN1, GOT1, HRG, IgE, IGF1, IL12p70, IL18, IL2, IL7, ITIH4, KITLG, KLK3, MMP2, RBP4, SAA4, SERPINF1, THPO, VCAM1 and VEGFA, to determine the level of the biomarkers in the sample. The levels of the biomarkers are compared to a standard to detect an increase or decrease in the level of each biomarker, thereby detecting and characterizing alcohol consumption in the subject. Each biomarker can be assayed in a separate aliquot of the sample. Alternatively, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 of the biomarkers can be assayed together in multiplex format Methods of detecting and characterizing alcohol consumption in a subject are provided according to aspects of the present invention which include assaying a subject sample for 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 or 38 biomarkers selected from: A1BG, A2M, ADIPQ, APCS1, APCS2, APOAI, APOC3, C3, C4a, C9, CALCA, CCL3, CCL4, CD40, CLU, CSF2, CXCL5, EGF, F3, F7, FABP3, FN1, GOT1, HRG, IgE, IGF1, IL12p70, IL18, IL2, IL7, KITLG, KLK3, MMP2, SAA4, SERPINF1, THPO, VCAM1 and VEGFA, to determine the level of the biomarkers in the sample. The levels of the assayed biomarkers are compared to a standard to detect an increase or decrease in the level of each assayed biomarker, thereby detecting and characterizing alcohol consumption in the subject. Each biomarker can be assayed in a separate aliquot of the sample. Alternatively, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 or 38 of the biomarkers can be assayed together in multiplex format Methods of detecting and characterizing alcohol consumption in a subject are provided according to aspects of the present invention which include assaying a subject sample for 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 biomarkers selected from: A1BG, A2M, ADIPQ, APCS1, APCS2, APOAI, APOC3, C3, C4a, C9, CALCA, CCL3, CCL4, CD40, CLU, CSF2, CXCL5, EGF, F3, F7, FABP3, FN1, GOT1, HRG, IgE, IGF1, IL12p70, IL18, IL2, IL7, ITIH4, KITLG, KLK3, MMP2, RBP4, SAA4, SERPINF1, THPO, VCAM1 and VEGFA, to determine the level of the biomarkers in the sample. The levels of the biomarkers are compared to a standard to detect an increase or decrease in the level of each biomarker, thereby detecting and characterizing alcohol consumption in the subject. Each biomarker can be assayed in a separate aliquot of the sample. Alternatively, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 of the biomarkers can be assayed together in multiplex format Methods of detecting and characterizing alcohol consumption in a subject are provided according to aspects of the present invention which include assaying a subject sample for 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 or 38 biomarkers selected from: A1BG, A2M, ADIPQ, APCS1, APCS2, APOAI, APOC3, C3, C4a, C9, CALCA, CCL3, CCL4, CD40, CLU, CSF2, CXCL5, EGF, F3, F7, FABP3, FN1, GOT1, HRG, IgE, IGF1, IL12p70, IL18, IL2, IL7, KITLG, KLK3, MMP2, SAA4, SERPINF1, THPO, VCAM1 and VEGFA, to determine the level of the biomarkers in the sample. The levels of the assayed biomarkers are compared to a standard to detect an increase or decrease in the level of each assayed biomarker, thereby detecting and characterizing alcohol consumption in the subject. Each biomarker can be assayed in a separate aliquot of the sample. Alternatively, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 or 38 of the biomarkers can be assayed together in multiplex format According to aspects of the present invention, the biomarkers are assayed by immunoassay.

According to aspects of the present invention, the biomarkers are assayed by a combination of gel electrophoresis and mass spectrometry.

According to aspects of the present invention, the biomarkers are assayed by liquid chromatography, mass spectrometry or a combination of liquid chromatography and mass spectrometry.

According to aspects of the present invention, the biomarkers are assayed by nucleic acid assay.

According to aspects of the present invention, the biomarkers are assayed by a nucleic acid assay selected from an amplification reaction; dot blot; in situ hybridization; Northern blot; and RNase protection.

Methods are provided according to aspects of the present invention wherein the subject is human.

Methods are provided according to aspects of the present invention wherein the subject is a non-human animal.

Methods are provided according to aspects of the present invention wherein the sample is blood plasma or blood serum.

Methods are provided according to aspects of the present invention wherein the sample is blood; a purified component of blood selected from the group consisting of red blood cells and white blood cells; urine, saliva; cerebrospinal fluid; a buccal sample; mucous; sweat; tears; semen; or amniotic fluid.

Methods are provided according to aspects of the present invention wherein the sample is a tissue biopsy.

Methods are provided according to aspects of the present invention wherein the tissue biopsy is a skin biopsy.

Methods of detecting and characterizing alcohol consumption in a subject are provided according to aspects of the present invention that include assaying a subject sample for a combination of 2, 3, 4, 5, 6, 7, 8, 9, 10, 11, 12, 13, 14, 15, 16 or 17 biomarkers of alcohol non-consumption, moderate consumption or high consumption selected from the group consisting of: ADIPQ, A2M, C3, CD40, CXCL5, F7, IgE, IGF1, IL2, IL7, CCL3, CCL4, MMP2, KLK3, GOT1, THPO and VEGFA, to determine the level of the 2, 3, 4, 5, 6, 7, 8, 9, 10, 11, 12, 13, 14, 15, 16 or 17 biomarkers in the sample and comparing the level of the 2, 3, 4, 5, 6, 7, 8, 9, 10, 11, 12, 13, 14, 15, 16 or 17 biomarkers in the sample to a standard, thereby detecting and characterizing alcohol consumption in the subject. Each biomarker can be assayed in a separate aliquot of the sample. Alternatively, 2, 3, 4, 5, 6, 7, 8, 9, 10, 11, 12, 13, 14, 15, 16 or 17 of the biomarkers can be assayed together in multiplex format.

Methods of detecting and characterizing alcohol consumption in a subject are provided according to aspects of the present invention that include assaying a subject sample for a combination of 3, 4, 5, 6, 7, 8, 9, 10, 11, 12, 13, 14, 15, 16 or 17 biomarkers of alcohol non-consumption, moderate consumption or high consumption selected from the group consisting of: ADIPQ, A2M, C3, CD40, CXCL5, F7, IgE, IGF1, IL2, IL7, CCL3, CCL4, MMP2, KLK3, GOT1, THPO and VEGFA, to determine the level of the 3, 4, 5, 6, 7, 8, 9, 10, 11, 12, 13, 14, 15, 16 or 17 biomarkers in the sample and comparing the level of the 3, 4, 5, 6, 7, 8, 9, 10, 11, 12, 13, 14, 15, 16 or 17 biomarkers in the sample to a standard, thereby detecting and characterizing alcohol consumption in the subject. Each biomarker can be assayed in a separate aliquot of the sample. Alternatively, 3, 4, 5, 6, 7, 8, 9, 10, 11, 12, 13, 14, 15, 16 or 17 of the biomarkers can be assayed together in multiplex format.

Methods of detecting and characterizing alcohol consumption in a subject are provided according to aspects of the present invention that include assaying a subject sample for a combination of 4, 5, 6, 7, 8, 9, 10, 11, 12, 13, 14, 15, 16 or 17 biomarkers of alcohol non-consumption, moderate consumption or high consumption selected from the group consisting of: ADIPQ, A2M, C3, CD40, CXCL5, F7, IgE, IGF1, IL2, IL7, CCL3, CCL4, MMP2, KLK3, GOT1, THPO and VEGFA, to determine the level of the 4, 5, 6, 7, 8, 9, 10, 11, 12, 13, 14, 15, 16 or 17 biomarkers in the sample and comparing the level of the 4, 5, 6, 7, 8, 9, 10, 11, 12, 13, 14, 15, 16 or 17 biomarkers in the sample to a standard, thereby detecting and characterizing alcohol consumption in the subject. Each biomarker can be assayed in a separate aliquot of the sample. Alternatively, 4, 5, 6, 7, 8, 9, 10, 11, 12, 13, 14, 15, 16 or 17 of the biomarkers can be assayed together in multiplex format.

Methods of detecting and characterizing alcohol consumption in a subject are provided according to aspects of the present invention that include assaying a subject sample for a combination of 5, 6, 7, 8, 9, 10, 11, 12, 13, 14, 15, 16 or 17 biomarkers of alcohol non-consumption, moderate consumption or high consumption selected from the group consisting of: ADIPQ, A2M, C3, CD40, CXCL5, F7, IgE, IGF1, IL2, IL7, CCL3, CCL4, MMP2, KLK3, GOT1, THPO and VEGFA, to determine the level of the 5, 6, 7, 8, 9, 10, 11, 12, 13, 14, 15, 16 or 17 biomarkers in the sample and comparing the level of the 5, 6, 7, 8, 9, 10, 11, 12, 13, 14, 15, 16 or 17 biomarkers in the sample to a standard, thereby detecting and characterizing alcohol consumption in the subject. Each biomarker can be assayed in a separate aliquot of the sample. Alternatively, 5, 6, 7, 8, 9, 10, 11, 12, 13, 14, 15, 16 or 17 of the biomarkers can be assayed together in multiplex format.

Methods of detecting alcohol consumption in a subject are provided according to aspects of the present invention that include assaying a subject sample for 2, 3, 4, 5, 6, 7, 8, 9, 10, 11, 12, 13 or 14 biomarkers selected from CD40, CXCL5, F7, IgE, IGF1, IL2, IL7, CCL3, CCL4, MMP2, KLK3, GOT1, THPO and VEGFA. The result of the assay can be compared to a standard to detect alcohol consumption in a subject. Each biomarker can be assayed in a separate aliquot of the sample. Alternatively, 2, 3, 4, 5, 6, 7, 8, 9, 10, 11, 12, 13 or 14 of the biomarkers can be assayed together in multiplex format.

Methods of detecting alcohol consumption in a subject are provided according to aspects of the present invention that include assaying a subject sample for 3, 4, 5, 6, 7, 8, 9, 10, 11, 12, 13 or 14 biomarkers selected from CD40, CXCL5, F7, IgE, IGF1, IL2, IL7, CCL3, CCL4, MMP2, KLK3, GOT1, THPO and VEGFA. The result of the assay can be compared to a standard to detect alcohol consumption in a subject. Each biomarker can be assayed in a separate aliquot of the sample. Alternatively, 3, 4, 5, 6, 7, 8, 9, 10, 11, 12, 13 or 14 of the biomarkers can be assayed together in multiplex format.

Methods of detecting alcohol consumption in a subject are provided according to aspects of the present invention that include assaying a subject sample for 4, 5, 6, 7, 8, 9, 10, 11, 12, 13 or 14 biomarkers selected from CD40, CXCL5, F7, IgE, IGF1, IL2, IL7, CCL3, CCL4, MMP2, KLK3, GOT1, THPO and VEGFA. The result of the assay can be compared to a standard to detect alcohol consumption in a subject. Each biomarker can be assayed in a separate aliquot of the sample. Alternatively, 4, 5, 6, 7, 8, 9, 10, 11, 12, 13 or 14 of the biomarkers can be assayed together in multiplex format.

Methods of detecting alcohol consumption in a subject are provided according to aspects of the present invention that include assaying a subject sample for 5, 6, 7, 8, 9, 10, 11, 12, 13 or 14 biomarkers selected from CD40, CXCL5, F7, IgE, IGF1, IL2, IL7, CCL3, CCL4, MMP2, KLK3, GOT1, THPO and VEGFA. The result of the assay can be compared to a standard to detect alcohol consumption in a subject. Each biomarker can be assayed in a separate aliquot of the sample. Alternatively, 5, 6, 7, 8, 9, 10, 11, 12, 13 or 14 of the biomarkers can be assayed together in multiplex format.

Methods of detecting alcohol consumption in a subject are provided according to aspects of the present invention that include assaying a subject sample for: CD40, CXCL5, F7, IgE, IGF1, IL2, IL7, CCL3, CCL4, MMP2, KLK3, GOT1, THPO and VEGFA. The result of the assay can be compared to a standard to detect alcohol consumption in a subject.

Methods of detecting and differentiating moderate alcohol consumption and heavy alcohol consumption in a subject are provided according to aspects of the present invention that include assaying a subject sample for at least one biomarker selected from ADIPOQ, A2M and C3, to determine the level of the biomarker in the sample; and comparing the level of the biomarker in the sample to a standard, thereby detecting and differentiating moderate alcohol consumption and heavy alcohol consumption in the subject.

Methods of detecting and differentiating moderate alcohol consumption and heavy alcohol consumption in a subject are provided according to aspects of the present invention that include assaying a subject sample for at least two biomarkers selected from ADIPOQ, A2M and C3, to determine the level of the biomarker in the sample; and comparing the level of the biomarker in the sample to a standard, thereby detecting and differentiating moderate alcohol consumption and heavy alcohol consumption in the subject.

Methods of detecting and differentiating moderate alcohol consumption and heavy alcohol consumption in a subject are provided according to aspects of the present invention that include assaying a subject sample for: ADIPOQ, A2M and C3, to determine the level of ADIPOQ, A2M and C3 biomarkers in the sample; and comparing the level of ADIPOQ, A2M and C3 in the sample to a standard, thereby detecting and differentiating moderate alcohol consumption and heavy alcohol consumption in the subject. Optionally, assay for additional biomarkers for detecting and differentiating moderate alcohol consumption and heavy alcohol consumption may be assayed.

Kits for detecting and characterizing alcohol consumption in a subject are provided according to aspects of the present invention that include a set of at least two binding partners, each binding partner specific for one of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 biomarkers selected from: A1BG, A2M, ADIPQ, APCS1, APCS2, APOAI, APOC3, C3, C4a, C9, CALCA, CCL3, CCL4, CD40, CLU, CSF2, CXCL5, EGF, F3, F7, FABP3, FN1, GOT1, HRG, IgE, IGF1, IL12p70, IL18, IL2, IL7, ITIH4, KITLG, KLK3, MMP2, RBP4, SAA4, SERPINF1, THPO, VCAM1 and VEGFA.

Kits for detecting and characterizing alcohol consumption in a subject are provided according to aspects of the present invention that include a set of at least two antibodies, aptamers or primers, each antibody, aptamer or primer specific for one of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 biomarkers selected from: A1BG, A2M, ADIPQ, APCS1, APCS2, APOAI, APOC3, C3, C4a, C9, CALCA, CCL3, CCL4, CD40, CLU, CSF2, CXCL5, EGF, F3, F7, FABP3, FN1, GOT1, HRG, IgE, IGF1, IL12p70, IL18, IL2, IL7, ITIH4, KITLG, KLK3, MMP2, RBP4, SAA4, SERPINF1, THPO, VCAM1 and VEGFA.

Kits for detecting and characterizing alcohol consumption in a subject are provided according to aspects of the present invention that include a set of at least three antibodies, aptamers or primers, each antibody, aptamer or primer specific for one of 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 biomarkers selected from: A1BG, A2M, ADIPQ, APCS1, APCS2, APOAI, APOC3, C3, C4a, C9, CALCA, CCL3, CCL4, CD40, CLU, CSF2, CXCL5, EGF, F3, F7, FABP3, FN1, GOT1, HRG, IgE, IGF1, IL12p70, IL18, IL2, IL7, ITIH4, KITLG, KLK3, MMP2, RBP4, SAA4, SERPINF1, THPO, VCAM1 and VEGFA.

Kits for detecting and characterizing alcohol consumption in a subject are provided according to aspects of the present invention that include a set of at least four antibodies, aptamers or primers, each antibody, aptamer or primer specific for one of 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 biomarkers selected from: A1BG, A2M, ADIPQ, APCS1, APCS2, APOAI, APOC3, C3, C4a, C9, CALCA, CCL3, CCL4, CD40, CLU, CSF2, CXCL5, EGF, F3, F7, FABP3, FN1, GOT1, HRG, IgE, IGF1, IL12p70, IL18, IL2, IL7, ITIH4, KITLG, KLK3, MMP2, RBP4, SAA4, SERPINF1, THPO, VCAM1 and VEGFA.

Kits for detecting and characterizing alcohol consumption in a subject are provided according to aspects of the present invention that include a set of at least five antibodies, aptamers or primers, each antibody, aptamer or primer specific for one of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 biomarkers selected from: A1BG, A2M, ADIPQ, APCS1, APCS2, APOAI, APOC3, C3, C4a, C9, CALCA, CCL3, CCL4, CD40, CLU, CSF2, CXCL5, EGF, F3, F7, FABP3, FN1, GOT1, HRG, IgE, IGF1, IL12p70, IL18, IL2, IL7, ITIH4, KITLG, KLK3, MMP2, RBP4, SAA4, SERPINF1, THPO, VCAM1 and VEGFA.

Kits for detecting and characterizing alcohol consumption in a subject are provided according to aspects of the present invention that include a set of at least two antibodies, aptamers or primers, each antibody, aptamer or primer specific for one of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 or 38 biomarkers selected from: A1BG, A2M, ADIPQ, APCS1, APCS2, APOAI, APOC3, C3, C4a, C9, CALCA, CCL3, CCL4, CD40, CLU, CSF2, CXCL5, EGF, F3, F7, FABP3, FN1, GOT1, HRG, IgE, IGF1, IL12p70, IL18, IL2, IL7, KITLG, KLK3, MMP2, SAA4, SERPINF1, THPO, VCAM1 and VEGFA.

Kits for detecting and characterizing alcohol consumption in a subject are provided according to aspects of the present invention that include a set of at least three antibodies, aptamers or primers, each antibody, aptamer or primer specific for one of 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 or 38 biomarkers selected from: A1BG, A2M, ADIPQ, APCS1, APCS2, APOAI, APOC3, C3, C4a, C9, CALCA, CCL3, CCL4, CD40, CLU, CSF2, CXCL5, EGF, F3, F7, FABP3, FN1, GOT1, HRG, IgE, IGF1, IL12p70, IL18, IL2, IL7, KITLG, KLK3, MMP2, SAA4, SERPINF1, THPO, VCAM1 and VEGFA.

Kits for detecting and characterizing alcohol consumption in a subject are provided according to aspects of the present invention that include a set of antibodies, aptamers or primers, each antibody, aptamer or primer specific for one of at least four 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 or 38 biomarkers selected from: A1BG, A2M, ADIPQ, APCS1, APCS2, APOAI, APOC3, C3, C4a, C9, CALCA, CCL3, CCL4, CD40, CLU, CSF2, CXCL5, EGF, F3, F7, FABP3, FN1, GOT1, HRG, IgE, IGF1, IL12p70, IL18, IL2, IL7, KITLG, KLK3, MMP2, SAA4, SERPINF1, THPO, VCAM1 and VEGFA.

Kits for detecting and characterizing alcohol consumption in a subject are provided according to aspects of the present invention that include a set of at least five antibodies, aptamers or primers, each antibody, aptamer or primer specific for one of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 or 38 biomarkers selected from: A1BG, A2M, ADIPQ, APCS1, APCS2, APOAI, APOC3, C3, C4a, C9, CALCA, CCL3, CCL4, CD40, CLU, CSF2, CXCL5, EGF, F3, F7, FABP3, FN1, GOT1, HRG, IgE, IGF1, IL12p70, IL18, IL2, IL7, KITLG, KLK3, MMP2, SAA4, SERPINF1, THPO, VCAM1 and VEGFA.

Kits for detecting and characterizing alcohol consumption in a subject are provided according to aspects of the present invention that include a set of at least two antibodies, aptamers or primers, each antibody, aptamer or primer specific for one of 2, 3, 4, 5, 6, 7, 8, 9, 10, 11, 12, 13, 14, 15, 16 or 17 biomarkers selected from: ADIPQ, A2M, C3, CD40, CXCL5, F7, IgE, IGF1, IL2, IL7, CCL3, CCL4, MMP2, KLK3, GOT1, THPO and VEGFA.

Kits for detecting and characterizing alcohol consumption in a subject are provided according to aspects of the present invention that include a set of at least three antibodies, aptamers or primers, each antibody, aptamer or primer specific for one of 3, 4, 5, 6, 7, 8, 9, 10, 11, 12, 13, 14, 15, 16 or 17 biomarkers selected from: ADIPQ, A2M, C3, CD40, CXCL5, F7, IgE, IGF1, IL2, IL7, CCL3, CCL4, MMP2, KLK3, GOT1, THPO and VEGFA.

Kits for detecting and characterizing alcohol consumption in a subject are provided according to aspects of the present invention that include a set of at least four antibodies, aptamers or primers, each antibody, aptamer or primer specific for one of 4, 5, 6, 7, 8, 9, 10, 11, 12, 13, 14, 15, 16 or 17 biomarkers selected from: ADIPQ, A2M, C3, CD40, CXCL5, F7, IgE, IGF1, IL2, IL7, CCL3, CCL4, MMP2, KLK3, GOT1, THPO and VEGFA.

Kits for detecting and characterizing alcohol consumption in a subject are provided according to aspects of the present invention that include a set of at least five antibodies, aptamers or primers, each antibody, aptamer or primer specific for one of 5, 6, 7, 8, 9, 10, 11, 12, 13, 14, 15, 16 or 17 biomarkers selected from: ADIPQ, A2M, C3, CD40, CXCL5, F7, IgE, IGF1, IL2, IL7, CCL3, CCL4, MMP2, KLK3, GOT1, THPO and VEGFA.

Kits for detecting and characterizing alcohol consumption in a subject are provided according to aspects of the present invention that include a set of at least one antibody, aptamer or primer, each antibody, aptamer or primer specific for one of ADIPOQ, A2M and C3.

Kits for detecting and characterizing alcohol consumption in a subject are provided according to aspects of the present invention that include a set of at least two antibodies, aptamers or primers, each antibody, aptamer or primer specific for one of ADIPOQ, A2M and C3.

Kits for detecting and characterizing alcohol consumption in a subject are provided according to aspects of the present invention that include a set of at least three antibodies, aptamers or primers, each antibody, aptamer or primer specific for one of ADIPOQ, A2M and C3.

BRIEF DESCRIPTION OF THE DRAWINGS

FIG. 5A is a diagram illustrating analysis of biomarkers and comparing alcohol abuse compared to no alcohol abuse;

FIG. 5B is a diagram illustrating analysis of biomarkers and comparing alcohol use compared to no alcohol use;

DETAILED DESCRIPTION OF THE INVENTION

Figure 1A:
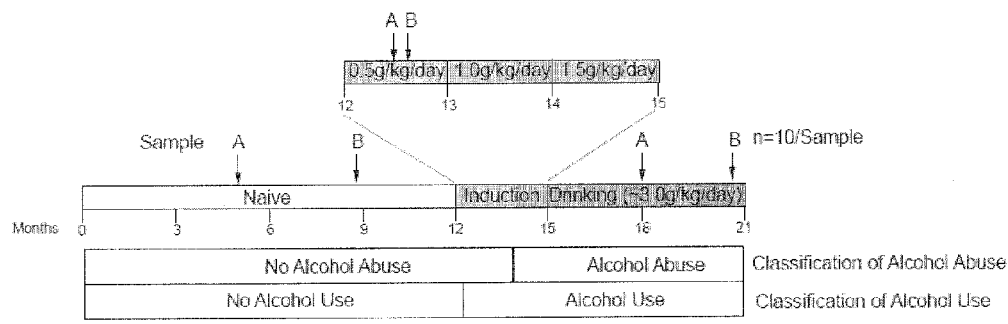
FIG. 1A is a schematic diagram of the phases of the training over a period of 21 months.

Scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W.H. Freeman & Company, 2004; and Herdewijn, P. (Ed.), Oligonucleotide Synthesis: Methods and Applications, Methods in Molecular Biology, Humana Press, 2004.

Methods and compositions are provided according to the present invention for detecting non-consumption, moderate consumption and high consumption of ethanol by a subject. Embodiments of the present invention relate to detection of a panel of plasma proteins for detecting non-consumption, moderate consumption and high consumption of ethanol by a subject.

A standard drink is equal to 13.7 grams (0.6 ounces) of pure alcohol. Examples of servings including an amount of alcohol equivalent to a standard drink are 12-ounces of beer, 8-ounces of malt liquor, 5-ounces of wine and 1.5-ounces or a "shot" of 80-proof distilled spirits or liquor. Moderate alcohol consumption in humans is generally defined as having no more than 1 drink per day for women and no more than 2 drinks per day for men. Heavy, or high, alcohol consumption for humans is generally defined as consuming an average of more than 2 drinks per day for men and more than 1 drink per day for women.

Non-human animal models of alcohol consumption are based on alcohol intake/unit body mass amounts proportionate to those defined for humans. Non-human primates share similar alcohol-related pathology to humans as described in Grant and Bennett, 2003, Pharmacology & Therapeutics 100, 235-255, but can be studied in a controlled environment and with the capacity for longitudinal within-subject examination. Monkeys also display alcohol absorption and metabolism pharmacokinetics similar to human beings as described in Green et al., 1999, Alcoholism: Clinical and Experimental Research 23, 611-616 and display commonalities with changes in human plasma proteins, see Freeman et al., 2006, Alcohol and Alcoholism 41, 300-305. These qualities make non-human primates a valuable model system for discovery of biomarkers indicative of non-consumption, moderate consumption and high consumption in humans, as well as other animals. Non-human primate models of chronic ethanol exposure in which animals self-administer large quantities of ethanol chronically over months or years are well-characterized as described in Grant et al., 2008, *Alcoholism: Clinical and Experimental Research* 32, 1824-1838; Grant et al., 2008, Alcohol Research and Health, 289-297; Ivester et al., 2007, Alcoholism: Clinical and Experimental Research 31, 144-155; Vivian et al., 2001, Alcoholism: Clinical and Experimental Research 25, 1087-1097.

Methods and compositions according to embodiments of the present invention are provided that specifically and sensitively detect alcohol consumption and whether alcohol consumption is moderate or high in a subject. Methods and compositions according to embodiments of the present invention find utility in, among other applications, clinical diagnostic tests to identify drinking behavior within individuals of a random population; monitoring of general drinking behavior in special populations; providing support surveillance for patients in alcohol abuse treatment programs to insure compliance; evaluating preclinical alcohol-related pathologies; and as surrogate markers of treatment efficacy, such as in clinical pharmacotherapeutic, behavioral therapeutic programs and social prevention programs.

Particular biomarkers included in a panel of biomarkers assayed according to embodiments of the present invention are selected from: Adiponectin (ADIPQ); Alpha-2 Macroglobulin (A2M); Apolipoprotein A1 (APOAI); Complement 3 (C3); Calcitonin (CALCA); CD40; chemokine (C-X-C motif) ligand 5 (CXCL5); Fatty Acid Binding Protein (FABP3); Factor VII (F7); IgE; insulin-like growth factor 1 (IGF1); interleukin-12p70 (IL12p70); interleukin-18 (IL18); interleukin-2 (IL2); interleukin-7 (IL7); chemokine (C-C motif) ligand 3 (CCL3); chemokine (C-C motif) ligand 4 (CCL4); matrix metallopeptidase 2 (MMP2); kallikrein-related peptidase 3 (KLK3); KIT ligand (KITLG); glutamic-oxaloacetic transaminase 1 (GOT1); coagulation factor III (F3); Thrombopoietin (THPO); vascular endothelial growth factor A (VEGFA); Apolipoprotein CIII (APOC3); epidermal growth factor (EGF); colony stimulating factor 2 (CSF2); vascular cell adhesion molecule 1 (VCAM1); complement 9 (C9); alpha 1B glycoprotein precursor (A1BG); Chain A, the structure of pentameric human serum amyloid P component (APCS1); Clusterin (CLU); complement C4A (C4a); fibronectin 1 isoform 6 preprotein (FN1); histidine rich glycoprotein precursor (HRG); interalpha inhibitor 4 (ITIH4); pigment epithelium-derived factor (SERPINF1); preserum amyloid P4 (APCS2); retinol binding protein 4 (RBP4); serum amyloid A4 (SAA4). Each of these proteins is well-known in the art in humans, non-human primates and in other animals.

Methods for detecting alcohol non-consumption, moderate consumption or high consumption in a subject are provided according to embodiments of the present invention which include assaying a subject sample for a combination of two or more biomarkers selected from the group consisting of: A1BG, A2M, ADIPQ, APCS1, APCS2, APOAI, APOC3, C3, C4a, C9, CALCA, CCL3, CCL4, CD40, CLU, CSF2, CXCL5, EGF, F3, F7, FABP3, FN1, GOT1, HRG, IgE, IGF1, IL12p70, IL18, IL2, IL7, ITIH4, KITLG, KLK3, MMP2, RBP4, SAA4, SERPINF1, THPO, VCAM1 and VEGFA.

Optionally 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 biomarkers selected from the group consisting of: A1BG, A2M, ADIPQ, APCS1, APCS2, APOAI, APOC3, C3, C4a, C9, CALCA, CCL3, CCL4, CD40, CLU, CSF2, CXCL5, EGF, F3, F7, FABP3, FN1, GOT1, HRG, IgE, IGF1, IL12p70, IL18, IL2, IL7, ITIH4, KITLG, KLK3, MMP2, RBP4, SAA4, SERPINF1, THPO, VCAM1 and VEGFA, are assayed in the sample in order to detect non-consumption, moderate consumption or high consumption in a subject.

In further embodiments, methods of detecting and differentiating alcohol non-consumption, moderate consumption and high consumption in a subject include assaying a subject sample for a combination of two or more biomarkers selected from the group consisting of: ADIPQ, A2M, C3, CD40, CXCL5, F7, IgE, IGF1, IL2, IL7, CCL3, CCL4, MMP2, KLK3, GOT1, THPO and VEGFA.

In still further embodiments, methods of detecting and differentiating alcohol non-consumption from moderate consumption or high consumption in a subject include assaying a subject sample for a combination of two or more biomarkers selected from the group consisting of: CD40, CXCL5, F7, IgE, IGF1, IL2, IL7, CCL3, CCL4, MMP2, KLK3, GOT1, THPO and VEGFA.

In yet further embodiments, methods of detecting and differentiating moderate alcohol consumption from high alcohol consumption in a subject include assaying a subject sample for at least one of: ADIPOQ, A2M and C3. In further embodiments, methods of detecting and differentiating moderate alcohol consumption from high alcohol consumption in a subject include assaying a subject sample for at least two of: ADIPOQ, A2M and C3. In still further embodiments, methods of detecting and differentiating moderate alcohol consumption from high alcohol consumption in a subject include assaying a subject sample for: ADIPOQ, A2M and C3.

A sample from any type of subject can be assayed, including non-human primates and other non-human animals. According to embodiments of the present invention, the subject is human.

In certain embodiments, the subject is a non-human animal. Methods for use in conjunction with a non-human animal detect non-human orthologs of the indicated biomarkers in a sample.

A sample can be a sample obtained from a subject, such as a bodily fluid illustratively including blood, blood plasma, blood serum, urine, saliva, cerebrospinal fluid, mucous, sweat, tears, semen, and amniotic fluid. A sample can be a tissue or organ sample, such as a skin biopsy or buccal swab. A sample can be a purified component of blood, such as red blood cells, white blood cells, blood plasma or blood serum. In some embodiments, a sample is blood plasma or blood serum.

A sample from a subject is optionally purified for assay according to a method of the present invention. The term "purified" in the context of a sample refers to separation of a biomarker from at least one other component present in the sample. The term "purified" encompasses separation of sample components to remove some or all of an undesired component of the sample. The term "purified" does not require absolute purity of a biomarker of the sample or complete removal of an undesired component and is intended as a relative term. For example, abundant materials, such as abundant proteins, may be entirely or partially removed from a sample to facilitate analysis of biomarkers.

A sample may be purified to remove some or all of an abundant protein selected from albumin, IgG, antitrypsin, IgA, transferrin, haptoglobin, fibrinogen, alpha2-macroglobulin, alpha 1-acid glycoprotein, IgM, apolipoprotein AI, apolipoprotein AII, complement C3, and transthyretin.

For example, a plasma sample may be purified to remove some or all of an abundant protein selected from albumin, IgG, antitrypsin, IgA, transferrin, haptoglobin, fibrinogen, alpha2-macroglobulin, alpha 1-acid glycoprotein, IgM, apolipoprotein AI, apolipoprotein AII, complement C3, and transthyretin.

Sample purification is achieved by well-known techniques illustratively including electrophoretic methods such as gel electrophoresis and 2-D gel electrophoresis; chromatography methods such as HPLC, ion exchange chromatography, affinity chromatography, size exclusion chromatography, thin layer and paper chromatography.

Methods of detecting and characterizing alcohol consumption in a subject according to embodiments of the present invention include assaying a subject sample for a combination of two or more biomarkers selected from the group: A1BG, A2M, ADIPQ, APCS1, APCS2, APOAI, APOC3, C3, C4a, C9, CALCA, CCL3, CCL4, CD40, CLU, CSF2, CXCL5, EGF, F3, F7, FABP3, FN1, GOT1, HRG, IgE, IGF1, IL12p70, IL18, IL2, IL7, ITIH4, KITLG, KLK3, MMP2, RBP4, SAA4, SERPINF1, THPO, VCAM1 and VEGFA, to determine the level of the two or more biomarkers in the sample Any assay methodology capable of detecting biomarkers described herein may be used, including, but not limited to, binding assays and spectroscopic methods, such as spectrometry and surface plasmon resonance. The phrase "determine the level" with respect to biomarkers assayed refers to the quantitative or qualitative measurement or analysis of the biomarker as well as to the detection of the presence or absence of the biomarker.

The two or more biomarkers can be assayed together in multiplex format or separately. The two or more biomarkers can be assayed simultaneously or a different times.

Methods are provided that further include assaying two or more biomarkers selected from A1BG, A2M, ADIPQ, APCS1, APCS2, APOAI, APOC3, C3, C4a, C9, CALCA, CCL3, CCL4, CD40, CLU, CSF2, CXCL5, EGF, F3, F7, FABP3, FN1, GOT1, HRG, IgE, IGF1, IL12p70, IL18, IL2, IL7, ITIH4, KITLG, KLK3, MMP2, RBP4, SAA4, SERPINF1, THPO, VCAM1 and VEGFA in a control sample and/or comparing an amount of the detected two or more biomarkers to a standard.

Standards are well-known in the art and the standard used can be any appropriate standard. In one example, a standard is an amount of the biomarker present in a comparable sample from a control subject. A standard may be a reference level of the biomarker or set of biomarkers previously determined in a sample of an individual subject or in a population and stored in a print or electronic medium for recall and comparison to an assay result.

A standard can be an amount of the biomarker present in a comparable sample obtained from the same subject at a different time. For example, a standard can be an amount of the biomarker present in a comparable sample obtained from the same subject at a different time. A first sample can be obtained from an individual subject at a first time to obtain a subject-specific baseline level of the biomarkers in the first sample. A second sample can be obtained from the individual subject at a second time and assayed for biomarkers to monitor differences in the levels of the biomarkers compared to the first sample, thereby monitoring alcohol intake in the subject.

Additional samples can be obtained from the subject at additional time points and assayed for biomarkers to monitor differences in the levels of the biomarkers compared to the first sample, second sample or other samples, thereby monitoring alcohol intake in the subject.

A standard can be an average level of a biomarker described herein present in comparable samples of one or more populations. The "average level" is determined by assay of the biomarker in comparable samples obtained from each member of the population. The term "comparable sample" is used to indicate that the samples are of the same type, i.e. each of the comparable samples is a plasma sample, for example.

A difference detected in levels of biomarkers in assays of the present invention compared to a standard can an increase or decrease in level of the biomarker. The increase or decrease is indicative of the state of the individual from whom the assayed sample was obtained and characterizes the individual as non-drinking, moderate drinking or heavy drinking as shown in FIGS. 2A, 2B, 2C, 4A-Q, 9A-E, 10A-C, 12 and 13 and Tables I, II, III and V. The magnitude of the increase or decrease can be, for example, at least 5%, 10%, 15%, 20%, 25%, 30%, 35%, 40%, 45%, 50%, 55%, 60%, 65%, 70%, 75%, 80%, 85%, 90%, 95%, 99%, or more, of the standard level.

Assay results can be analyzed using statistical analysis by any of various methods, exemplified by parametric or non-parametric tests, analysis of variance, analysis of covariance, logistic regression for multivariate analysis, Fisher's exact test, the chi-square test, Student's T-test, the Mann-Whitney test, Wilcoxon signed ranks test, McNemar test, Friedman test and Page's L trend test. These and other statistical tests are well-known in the art as detailed in Hicks, C M, Research Methods for Clinical Therapists: Applied Project Design and Analysis, Churchill Livingstone (publisher); $5^{th}$ Ed., 2009; and Freund, R J et al., Statistical Methods, Academic Press; $3^{rd}$ Ed., 2010.

In one embodiment, methods are provided which include assaying two or more biomarkers selected from A1BG, A2M, ADIPQ, APCS1, APCS2, APOAI, APOC3, C3, C4a, C9, CALCA, CCL3, CCL4, CD40, CLU, CSF2, CXCL5, EGF, F3, F7, FABP3, FN1, GOT1, HRG, IgE, IGF1, IL12p70, IL18, IL2, IL7, ITIH4, KITLG, KLK3, MMP2, RBP4, SAA4, SERPINF1, THPO, VCAM1 and VEGFA in a sample obtained from a subject to determine the level of the two or more biomarkers. The level of the two or more biomarkers in the sample obtained from the subject is compared to the average level of the two or more biomarkers in a population of individuals characterized by alcohol non-consumption, moderate consumption or high consumption, to determine whether the subject is characterized by alcohol non-consumption, moderate consumption or high consumption.

In an exemplary embodiment, methods are provided which include assaying ADIPOQ, A2M and C3 in a sample obtained from a subject to determine the level of ADIPOQ, A2M and C3 in the sample. The level of ADIPOQ, A2M and C3 in the sample obtained from the subject is compared to the average level of ADIPOQ, A2M and C3 in a population of individuals characterized by alcohol non-consumption, moderate consumption or high consumption, to determine whether the subject is characterized by alcohol non-consumption, moderate consumption or high consumption, wherein decreased levels of ADIPOQ, A2M and C3 in the subject sample compared to the average level in the population indicate moderate consumption or high consumption of alcohol by the subject.

Methods according to embodiments of the present invention include assaying a sample for biomarkers by a binding assay. A binding assay is an assay in which at least one biomarker is detected by binding of the biomarker with a binding partner. The term "binding partner" refers to a biological molecule capable of specific binding to a biomarker. Non-limiting examples of binding partners include antibodies, aptamers, receptors, ligands and substrates for enzymatic action of a biomarker. Binding partners may also be nucleic acid probes. The skilled artisan can routinely identify, isolate and/or make binding partners and use them in binding assays. Such techniques are well-known to those of ordinary skill in the art.

A binding assay can be performed according to any of various methods that allow for detection of a biomarker by binding to a binding partner. Binding of a biomarker and binding agent can be detected directly or indirectly using well-known detectable labels and detection methodology.

Detecting binding between a biomarker present in a sample and a binding partner is achieved by any of various methods known in the art, illustratively including detection of a detectable label directly or indirectly attached to the biomarker or the binding partner. The term "detectable label" refers to a material capable of producing a signal indicative of the presence of the detectable label by any appropriate method illustratively including spectroscopic, optical, photochemical, biochemical, enzymatic, electrical and/or immunochemical. Examples of detectable labels illustratively include a fluorescent moiety, a chemiluminescent moiety, a bioluminescent moiety, an electron dense particle, a magnetic particle, an enzyme, a substrate, a radioisotope and a chromophore.

The identity of a particular detectable label or labels used depends on the detection process used. Such detection processes are incorporated in particular assay formats illustratively including ELISA, Western blot, immunoprecipitation, immunocytochemistry, immuno-fluorescence assay, liquid chromatography, flow cytometry, other detection processes known in the art, or combinations thereof.

A binding assay can incorporate a binding partner attached to a support. A support with attached binding partner used in a binding assay can be solid or semi-solid and can be any of various materials such as glass, silicon, paper, a synthetic or naturally occurring polymer, such as polystyrene, polycarbonate, polypropylene, PVDF, nylon, cellulose, agarose, dextran, and polyacrylamide or any other material to which a binding partner can be stably attached for use in a binding assay.

A support used can include functional groups for binding to binding partners, such as, but not limited to carboxyl, amine, amino, carboxylate, halide, ester, alcohol, carbamide, aldehyde, chloromethyl, sulfur oxide, nitrogen oxide, epoxy and/or tosyl functional groups. Attachment of binding partners to a support is achieved by any of various methods, illustratively including adsorption and chemical bonding. In one example, 1-Ethyl-3-[3-dimethylaminopropyl]carbodiimide hydrochloride, EDC or EDAC chemistry, can be used to attach binding partners to particles. The binding partners can be bonded directly or indirectly to the material of the support, for example, via bonding to a coating or linker disposed on the support. Functional groups, modification thereof and attachment of a binding partner to a support are known in the art, for example as described in Fitch, R. M., Polymer Colloids: A Comprehensive Introduction, Academic Press, 1997.

Such supports can be in any of a variety of forms and shapes including, but not limited to, microtiter plates, microtiter wells, pins, fibers, beads, slides, silicon chips and membranes such as a nitrocellulose or PVDF membrane.

According to embodiments, a binding partner is attached to a support which is in the form of a particle. Such particles can be solid or semi-solid particles of any of a variety of shapes and sizes. Particles are illustratively organic or inorganic particles, such as glass or metal and can be particles of a synthetic or naturally occurring polymer, such as polystyrene, polycarbonate, silicon, nylon, cellulose, agarose, dextran, and polyacrylamide. Particles are latex beads in particular embodiments. Microparticles, such as microbeads, used can have a diameter of less than one millimeter, for example, a size ranging from about 0.1 to about 1,000 micrometers in diameter, inclusive. Nanoparticles, such as nanobeads used can have a diameter from about 1 nanometer (nm) to about 1,000 nm in diameter, inclusive. In certain embodiments, particles used are beads, such as microbeads and nanobeads.

Particles with attached binding partners for use in assays according to embodiments of the present invention can be encoded particles distinguishable from other particles based on a characteristic illustratively including an optical property such as color, reflective index and/or an imprinted or otherwise optically detectable pattern. For example, the particles may be encoded using optical, chemical, physical, or electronic tags.

Encoding of a particle can be embedded, for example, within the interior of the particle, or otherwise attached to the particle in a manner that is stable through the assay and analysis process. The code can be provided by any detectable means, such as by holographic encoding, by a fluorescence property, color, shape, size, light emission, quantum dot emission and the like to identify particle and thus the capture probes immobilized thereto. Optical bar codes can be used to encode particles.

Encoded beads for attachment of binding partners and methods of their generation and use are described, for example, in U.S. Pat. Nos. 5,981,180; 5,028,545; 4,499,052; and 6,916,661; U.S. Patent Application Publications 20040179267; 20040132205; 20040130786; 20040130761; 20040126875; 20040125424; and 20040075907 describe exemplary particles encoded by holographic barcodes. Commercially available encoded particle assay platforms can be used such as VeraCode beads and BeadXpress system (Illumina Inc., San Diego Calif.); and xMAP 3D (Luminex).

Particle supports are typically evaluated individually to detect binding of a binding partner and biomarker, such as by flow cytometry. In addition to flow cytometry, a centrifuge may be used as the instrument to separate and classify the particles, such as described in U.S. Pat. No. 5,926,387. A free-flow electrophoresis apparatus may be used to separate and classify the particles such as described in U.S. Pat. No. 4,310,408. The particles may also be placed on a surface and scanned or imaged.

Binding assays include, but are not limited to, immunoassays. Particular methods of immunoassay are known in the art and illustratively include enzyme-linked immunosorbent assay (ELISA), immunoblot, immunoprecipitation, immunocytochemistry, and radioimmunoassay. Assay methods may be used to obtain qualitative and/or quantitative results. Specific details of suitable assay methods for both qualitative and quantitative assay of a sample are described herein and in standard references, illustratively including E. Harlow and D. Lane, Antibodies: A Laboratory Manual, Cold Spring Harbor Laboratory Press, 1988; F. Breitling and S. Dike', Recombinant Antibodies, John Wiley & Sons, New York, 1999; H. Zola, Monoclonal Antibodies: Preparation and Use of Monoclonal Antibodies and Engineered Antibody Derivatives, Basics: From Background to Bench, BIOS Scientific Publishers, 2000; B. K. C. Lo, Antibody Engineering Methods and Protocols, Methods in Molecular Biology, Humana Press, 2003; F. M. Ausubel et al., Eds., Short Protocols in Molecular Biology, Current Protocols, Wiley, 2002; S. Klussman, Ed., The Aptamer Handbook: Functional Oligonucleotides and Their Applications, Wiley, 2006; Onnerod, M. G., Flow Cytometry: a practical approach, Oxford University Press, 2000; Givan, A. L., Flow Cytometry: first principles, Wiley, New York, 2001; Gorczyca, W., Flow Cytometry in Neoplastic Hematology: morphologic-immunophenotypic correlation, Taylor & Francis, 2006; and J. Sambrook and D. W. Russell, Molecular Cloning: A Laboratory Manual, Cold Spring Harbor Laboratory Press, 3rd Ed., 2001.

Antibodies and methods for preparation of antibodies are well-known in the art. As used herein, the terms "antibody" and "antibodies" encompass monoclonal antibodies, polyclonal antibodies, bispecific antibodies, multispecific antibodies, human antibodies, humanized antibodies, chimeric antibodies, camelized antibodies, single domain antibodies, single-chain Fvs (scFv), single chain antibodies, disulfide-linked Fvs (sdFv), and anti-idiotypic (anti-Id) antibodies and antigen-binding fragments of any of the above. In particular, antibodies include immunoglobulin molecules and immunologically active fragments of immunoglobulin molecules, i.e., molecules that contain an antigen binding site. Immunoglobulin molecules are of any type (e.g., IgG, IgE, IgM, IgD, IgA and IgY), class (e.g., IgG1, IgG2, IgG3, IgG4, IgA1 and IgA2), or subclass.

As used herein, the terms "antibody fragment" and "antigen-binding fragment" defines a fragment of an antibody that immunospecifically binds to a target biomarker. Antibody fragments may be generated by any technique known to one of skill in the art. For example, Fab and F(ab')$_2$ fragments may be produced by proteolytic cleavage of immunoglobulin molecules, using enzymes such as papain (to produce Fab fragments) or pepsin (to produce F(ab')$_2$ fragments). Antibody fragments are also produced by recombinant DNA technologies.

Antibodies, antigen-binding fragments, methods for their generation and methods for screening of generated antibodies for substantially specific binding to an antigen are known in the art and such antibodies, antigen binding fragments and methods are described in further detail, for instance, in Antibody Engineering, Kontermann, R. and Dübel, S. (Eds.), Springer, 2001; Harlow, E. and Lane, D., Antibodies: A Laboratory Manual, Cold Spring Harbor Laboratory Press, 1988; F. Breitling and S. Dübel, Recombinant Antibodies, John Wiley & Sons, New York, 1999; H. Zola, Monoclonal Antibodies: Preparation and Use of Monoclonal Antibodies and Engineered Antibody Derivatives, Basics: From Background to Bench, BIOS Scientific Publishers, 2000; Ausubel, F. et al., (Eds.), Short Protocols in Molecular Biology, Wiley, 2002; J. D. Pound (Ed.) Immunochemical Protocols, Methods in Molecular Biology, Humana Press, 2nd ed., 1998; B. K. C. Lo (Ed.), Antibody Engineering: Methods and Protocols, Methods in Molecular Biology, Humana Press, 2003; and Kohler, G. and Milstein, C., Nature, 256:495-497 (1975). Antibodies for biomarkers can be obtained commercially.

Aptamers can be used to assay biomarkers. The term "aptamer" refers to a peptide and/or nucleic acid that substantially specifically binds to a specified substance. In the case of a nucleic acid aptamer, the aptamer is characterized by binding interaction with a target other than Watson/Crick base pairing or triple helix binding with a second and/or third nucleic acid. Such binding interaction may include Van der Waals interaction, hydrophobic interaction, hydrogen bonding and/or electrostatic interactions, for example. Similarly, peptide-based aptamers are characterized by specific binding to a target wherein the aptamer is not a naturally occurring ligand for the target. Techniques for identification and generation of peptide and nucleic acid aptamers and their use are known in the art as described, for example, in F. M. Ausubel et al., Eds., Short Protocols in Molecular Biology, Current Protocols, Wiley, 2002; S. Klussman, Ed., The Aptamer Handbook: Functional Oligonucleotides and Their Applications, Wiley, 2006; and J. Sambrook and D. W. Russell, Molecular Cloning: A Laboratory Manual, Cold Spring Harbor Laboratory Press, 3rd Ed., 2001.

Any of various spectroscopy methods can be used to assay biomarkers according to embodiments of the present invention, including, but not limited to, gas chromatography, liquid chromatopgraphy, ion mobility spectrometry, mass spectrometry, liquid chromatography-mass spectrometry (LC-MS or HPLC-MS), ion mobility spectrometry-mass spectrometry, tandem mass spectrometry, gas chromatography-mass spectrometry, matrix-assisted desorption ionization time-of-flight (MALDI-TOF) mass spectrometry, surface-enhanced laser desorption ionization (SELDI) and nuclear magnetic resonance spectroscopy, all of which are well-known to the skill artisan.

Mass spectrometry analysis can be used in an assay according to embodiments of the present invention. Mass spectrometry analysis is conducted using, for example, time-of-flight (TOF) mass spectrometry, ion trap mass spectrometry, or Fourier transform ion cyclotron resonance mass spectrometry. Protein quantification can be achieved using such diverse methods as, spectral counting, accurate mass tagging, multiple reaction monitoring, and isobaric tagging. Mass spectrometry techniques are known in the art and exemplary detailed descriptions of methods for protein and/or peptide assay are found in Li J., et al., Clin Chem., 48(8):1296-304, 2002; Hortin, G. L., Clinical Chemistry 52: 1223-1237, 2006; Hortin, G. L., Clinical Chemistry 52: 1223-1237, 2006; A. L. Burlingame, et al. (Eds.), Mass Spectrometry in Biology and Medicine, Humana Press, 2000; and D. M. Desiderio, Mass Spectrometry of Peptides, CRC Press, 1990.

In one aspect, nucleic acids encoding the two or more biomarkers selected from the group: A1BG, A2M, ADIPQ, APCS1, APCS2, APOAI, APOC3, C3, C4a, C9, CALCA, CCL3, CCL4, CD40, CLU, CSF2, CXCL5, EGF, F3, F7, FABP3, FN1, GOT1, HRG, IgE, IGF1, IL12p70, IL18, IL2, IL7, ITIH4, KITLG, KLK3, MMP2, RBP4, SAA4, SERPINF1, THPO, VCAM1 and VEGFA, are assayed to determine their level compared to a standard.

Nucleic acid assays, include, but are not limited to, amplification reactions such as polymerase chain reactions (PCR), such as RT-PCR; dot blot; in situ hybridization; Northern blot; and RNase protection. Details of such assays are described in J. Sambrook and D. W. Russell, Molecular Cloning: A Laboratory Manual, Cold Spring Harbor Laboratory Press; 3rd Ed., 2001; and F. M. Ausubel, Ed., Short Protocols in Molecular Biology, Current Protocols; 5th Ed., 2002, for example.

According to embodiments of the present invention, a binding partner is a nucleic acid probe or primer able to hybridize to a target biomarker mRNA or cDNA to detect and/or quantify mRNA or cDNA encoding the biomarker. A nucleic acid probe can be an oligonucleotide of at least 10, 15, 30, 50 or 100 nucleotides in length and sufficient to specifically hybridize under stringent conditions to a biomarker mRNA or cDNA or complementary sequence thereof. A nucleic acid primer can be an oligonucleotide of at least 10, 15 or 20 nucleotides in length and sufficient to specifically hybridize under stringent conditions to the mRNA or cDNA, or complementary sequence thereof. The terms "specific hybridization" and "specifically hybridizes" refer to hybridization of a particular nucleic acid to a target nucleic acid without substantial hybridization to nucleic acids other than the target nucleic acid in a sample.

Stringency of hybridization and washing conditions depends on several factors, including the Tm of the probe and target and ionic strength of the hybridization and wash conditions, as is well-known to the skilled artisan. Hybridization and conditions to achieve a desired hybridization stringency are described, for example, in Sambrook et al., Molecular Cloning: A Laboratory Manual, Cold Spring Harbor Laboratory Press, 2001; and Ausubel, F. et al., (Eds.), Short Protocols in Molecular Biology, Wiley, 2002.

An example of high stringency hybridization conditions is hybridization of nucleic acids over about 100 nucleotides in length in a solution containing 6×SSC, 5×Denhardt's solution, 30% formamide, and 100 micrograms/ml denatured salmon sperm at 37° C. overnight followed by washing in a solution of 0.1×SSC and 0.1% SDS at 60° C. for 15 minutes. SSC is 0.15M NaCl/0.015M Na citrate. Denhardt's solution is 0.02% bovine serum albumin/0.02% FICOLL/0.02% polyvinylpyrrolidone.

A sample assayed for biomarker nucleic acids can be a sample obtained from a subject. A sample assayed for biomarker nucleic acids illustratively includes blood, blood plasma, blood serum, urine, saliva, cerebrospinal fluid, mucous, sweat, tears, semen, amniotic fluid, a tissue or organ sample, such as a skin biopsy or buccal swab. A sample can be a purified component of blood, such as red blood cells, white blood cells, blood plasma or blood serum.

A sample from a subject is optionally purified for assay according to a method of the present invention. Methods for isolation of mRNA and/or generation of cDNA for use in an assay of particular sequences are well known in the art.

Assay of a biomarker nucleic acid can be achieved using an in vitro amplification method. The term "amplification method" refers to a method for copying a template biomarker nucleic acid, thereby producing nucleic acids which include copies of all or a portion of the template biomarker nucleic acid.

Amplification methods included in embodiments of the present invention are those which include template directed primer extension catalyzed by a nucleic acid polymerase using a pair of primers which flank the target nucleic acid, illustratively including, but not limited to, Polymerase Chain Reaction (PCR), reverse-transcription PCR (RT-PCR). ligation-mediated PCR (LM-PCR), phi-29 PCR, and other nucleic acid amplification methods, for instance, as described in C. W. Dieffenbach et al., PCR Primer: A Laboratory Manual, Cold Spring Harbor Laboratory Press, 2003; and V. Demidov et al., DNA Amplification: Current Technologies and Applications, Taylor & Francis, 2004. The term "primer" refers to a single stranded oligonucleotide, typically about 10-60 nucleotides in length, that may be longer or shorter, and that serves as a point of initiation for template-directed DNA synthesis. Design of oligonucleotide primers suitable for use in amplification reactions is well known in the art, for instance as described in A. Yuryev et al., PCR Primer Design, Humana Press, 2007; C. W. Dieffenbach et al., PCR Primer: A Laboratory Manual, Cold Spring Harbor Laboratory Press, 2003; and V. Demidov et al., DNA Amplification: Current Technologies and Applications, Taylor & Francis, 2004. Appropriate reactions conditions for amplification methods include presence of suitable reaction components including, but not limited to, a polymerase and nucleotide triphosphates. One of skill in the art will be able to determine conditions suitable for amplification of the biomarker nucleic acids with only routine experimentation including choice of factors such as length of an included primer, buffer, nucleotides, pH, Mg salt concentration and temperature. The nucleic acid product of the amplification methods optionally contains additional materials such as, but not limited to, non-biomarker nucleic acid sequences, functional groups for chemical reaction and detectable labels, present in the primers and not present in the original DNA template.

Embodiments of kits according to the present invention optionally include one or more components for use in an assay of the present invention such as a binding partner, exemplified by an antibody or aptamer, a liquid such as a buffer and/or solution used in an assay, a container, a detectable label for labeling a binding partner, such as an antibody or aptamer, directly or indirectly, a standard, a negative control and a positive control. In preferred embodiments, a kit of the present invention includes at least two or more antibodies or aptamers specific for at least two or more biomarkers described herein.

In embodiments of kits of the present invention for detecting non-consumption, moderate consumption or high consumption of alcohol in a subject, a set of antibodies and/or aptamers directed to two or more biomarkers is included, the biomarkers selected from: A1BG, A2M, ADIPQ, APCS1, APCS2, APOAI, APOC3, C3, C4a, C9, CALCA, CCL3, CCL4, CD40, CLU, CSF2, CXCL5, EGF, F3, F7, FABP3, FN1, GOT1, HRG, IgE, IGF1, IL12p70, IL18, IL2, IL7, ITIH4, KITLG, KLK3, MMP2, RBP4, SAA4, SERPINF1, THPO, VCAM1 and VEGFA.

In further embodiments, kits of the present invention for detecting non-consumption, moderate consumption or high consumption of alcohol in a subject include a set of antibodies and/or aptamers directed to 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 biomarkers selected from: A1BG, A2M, ADIPQ, APCS1, APCS2, APOAI, APOC3, C3, C4a, C9, CALCA, CCL3, CCL4, CD40, CLU, CSF2, CXCL5, EGF, F3, F7, FABP3, FN1, GOT1, HRG, IgE, IGF1, IL12p70, IL18, IL2, IL7, ITIH4, KITLG, KLK3, MMP2, RBP4, SAA4, SERPINF1, THPO, VCAM1 and VEGFA.

In one aspect of the present invention, an array of biomarker binding partners is provided for use in an assay of biomarkers. Binding partners for two or more biomarkers are arrayed on a solid support such as, but not limited to, a membrane, glass, plastic, silicon or other support material. Binding partners are generally deposited on the support in an orderly addressable arrangement to facilitate identification of binding of biomarkers to the binding partners.

Embodiments of inventive compositions and methods are illustrated in the following examples. These examples are provided for illustrative purposes and are not considered limitations on the scope of inventive compositions and methods.

EXAMPLES

Example 1

Experiments were performed using a highly controlled monkey model of alcohol abuse to identify biomarkers of non-consumption as well as biomarkers of moderate consumption and/or high consumption in a subject. Over 1,000 different plasma proteins were monitored to detect biomarkers of the drinking state. Ten male cynomolgus monkeys (*macaca fascicularis*), are part of a 21-month experimental time line (FIG. 1A). For the first year (Naïve samples), monkeys, 5-6 years of age (average weight 4.5 kg), are acclimatized to the study environment and operant instrumentation. During this acclimatization period, the monkeys are also trained to present their leg for venipuncture to collect blood from the saphenose and/or femoral veins without the use of an anesthetic agent. Plasma samples are collected for endocrine tests, monitoring of blood alcohol levels, and for biomarker discovery and validation. Monkeys are induced to consume liquids under a schedule of food pellet deliveries (i.e., schedule-induced polydipsia as described in Falk, 1961, Science 133, 195-196), as described in Grant et al., 2008, Alcoholism: Clinical and Experimental Research 32, 1824-1838. Induction conditions did not require food deprivation and are not associated with weight loss. The ethanol is presented in the form of 4% w/v ethanol. Following one month of 0.5 g/kg/day ethanol (two drink equivalents, Induction samples), the animals are escalated to drink 1.0 g/kg/day for 30 consecutive days, and finally, 1.5 g/kg/day for 30 consecutive days. Following the 90-day induction period of alcohol consumption, animals are given unlimited access (22 hours per day) to either ethanol or water for the next six months (Drinking samples) as described in Grant et al., 2008, Alcoholism: Clinical and Experimental Research 32, 1824-1838; and Vivian et al., 2001, Alcoholism: Clinical and Experimental Research 25, 1087-1097). Two independent samples (A and B) are collected from each state in the experimental time line (Naïve, Induction, Drinking). These two independent samples are collected on different days to determine reproducibility of the plasma protein concentrations. FIG. 1A is a diagrammatic representation of the time course of non-human primate alcohol self-administration and plasma sampling points. Two independent samples (A and B) are collected from each condition (Naïve, Induction, and Drinking) for biomarker discovery and classification analysis testing.

Ethanol Self-Administration

Figure 1B:
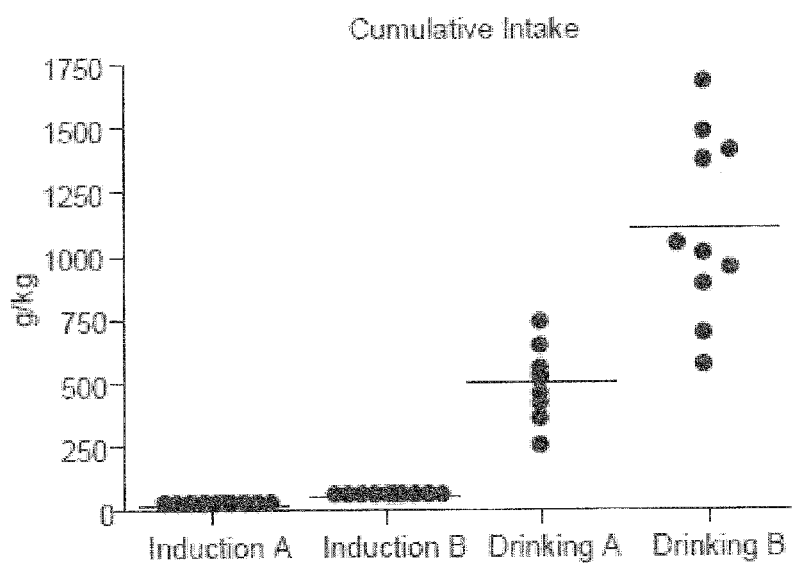
FIGS. 1B and 1C are graphs indicating the amount of alcohol consumed by monkeys during different phases of the experiments.
Figures 1C, 2A:
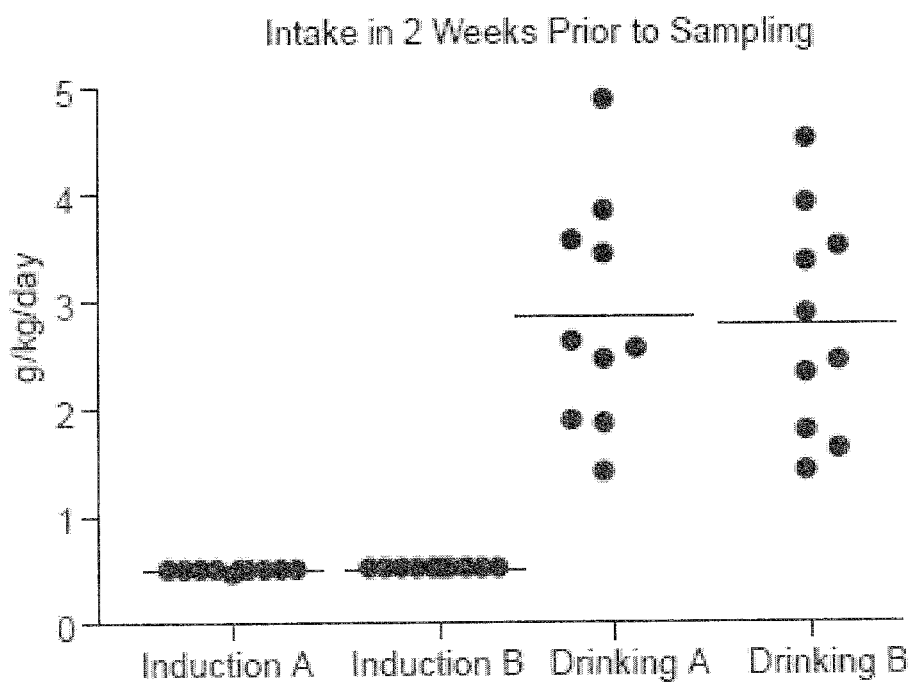
FIGS. 2A and 2B show identifying biomarkers of non-consumption, moderate consumption or high consumption.

The cumulative intake for these animals at the collection time points is presented in FIG. 1B. With chronic and compulsive drinking, there is naturally a higher total level of total consumption. During the 2 weeks prior to sample collection for the A and B Drinking samples, however, the level of alcohol consumption is not significantly different (FIG. 1C). FIG. 1C is a graph showing that in the two weeks prior to plasma sampling time points, the average daily intake is the same for A and B samples in the Induction or Drinking states. Data are presented with mean lines and dots for each animal and time point (n=10 for each sample). There is a tightly controlled 0.5 g/kg/day (2 drink equivalents per day) consumption during the initial month of ethanol induction which resulted in blood ethanol levels between 20-40 mg/dL depending on the drinking typography as described in Grant et al., 2008, Alcoholism: Clinical and Experimental Research 32, 1824-1838. The two Drinking time points (following 3 and 6 months of 22/hr/day access) had essentially the same amount of ethanol intake over the two weeks preceding sample collection when given unlimited assess (ca. 3 g/kg/day; approximately 12 drink equivalents per day).

Figure 3:
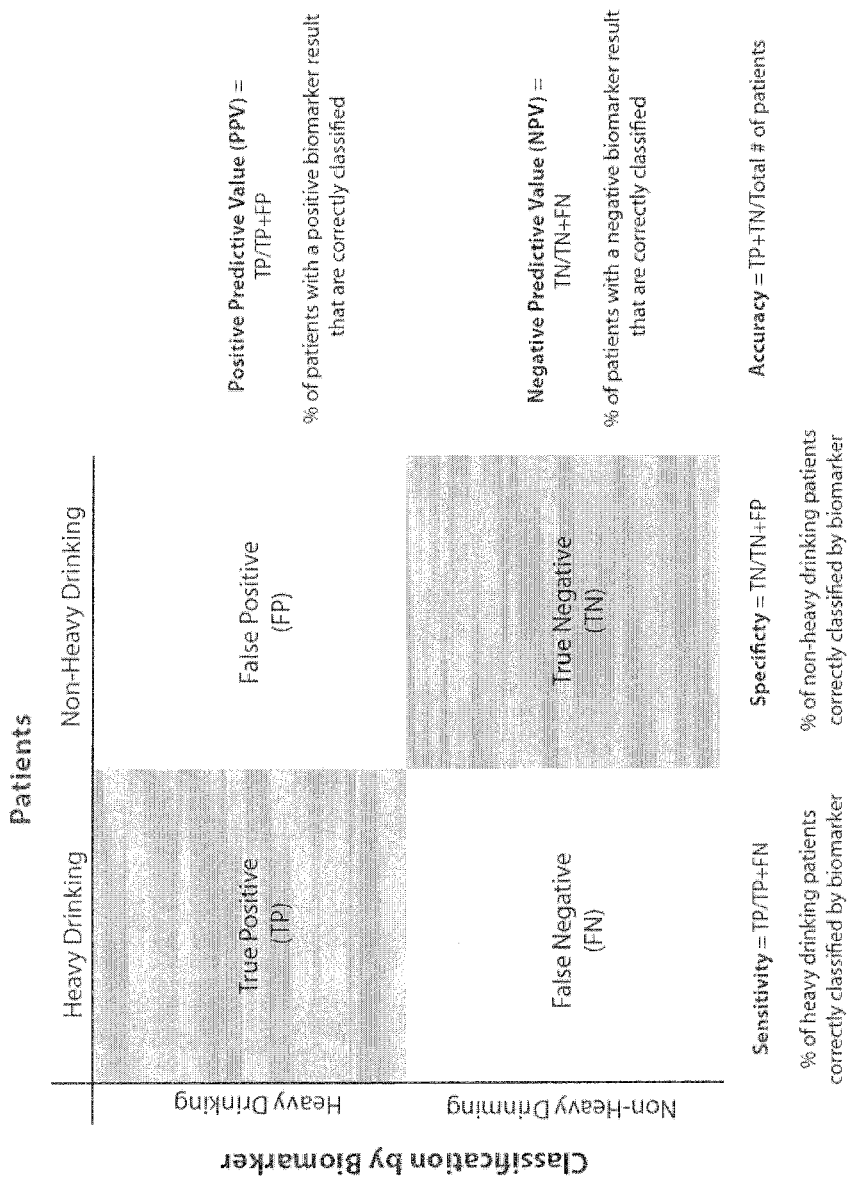
FIG. 3 is a diagram illustrating metrics for assessing biomarkers.

Plasma protein profiling is performed using standard Luminex technology as described in Vignali, D. A., 2000, J. Immunol. Methods, 243:243-255. Plasma samples (in triplicate) are subjected to Human Antigen MAP antigen analysis for 90 different circulating proteins. Sample and capture microspheres are thoroughly mixed and incubated at room temperature for 1 hour. Multiplexed cocktails of biotinylated reporter antibodies are then added and incubated for 1 hour. Multiplexes are developed using an excess of streptavidin-phycoerythrin solution. Analysis is performed in a Luminex 100 instrument. Unknown values for each of the analytes localized in a specific multiplex are determined using 4 and 5 parameter, weighted and non-weighted curve fitting algorithms included in the data analysis package. Differential abundance of individual plasma proteins is determined using a conservative approach with a One-Way repeated measures ANOVA and Bonferroni multiple testing correction (p<0.05). To identify the most consistent plasma protein changes, only those differences significant by a Student Newman-Keuls pair-wise post-hoc test (p<0.05) between two time points and for both the A and B samples are considered. Support Vector Machine (SVM) classification analysis is performed using GeneSpring 7.3 (Agilent) using a polynomial kernel function with no scaling factor as described in Freeman, W. M. et al., Pharmacogenomics J., 2010, 10(5):385-95. A statistical tool only recently applied to biomedical research, SVM is a supervised machine learning method that allows for classification of samples based on a hyperplane constructed in n-dimensional space where n is the number of quantitative measures. In this study, the plasma concentrations of the proteins in the biomarker panel are used to classify drinking status. Accuracy, sensitivity, specificity, PPV (positive predictive value), and NPV (negative predictive value) are determined according to standard definitions from classification analysis results as described in Freeman and Vrana, Alcohol Clin Exp Res. 2010 June; 34(6):946-54 and results are shown in FIG. 3. Database searching for tissue origin of proteins is performed using Ingenuity Pathway Analysis software and Swissprot identifiers (Ingenuity, Redwood City Calif.).

Biomarker Analysis

Figure 4A:
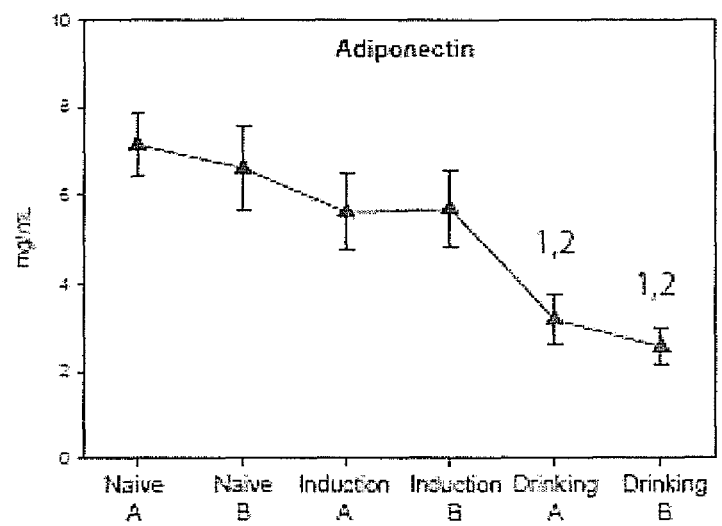
FIG. 4A is a graph showing adiponectin plasma expression across drinking states.
Figure 4B:
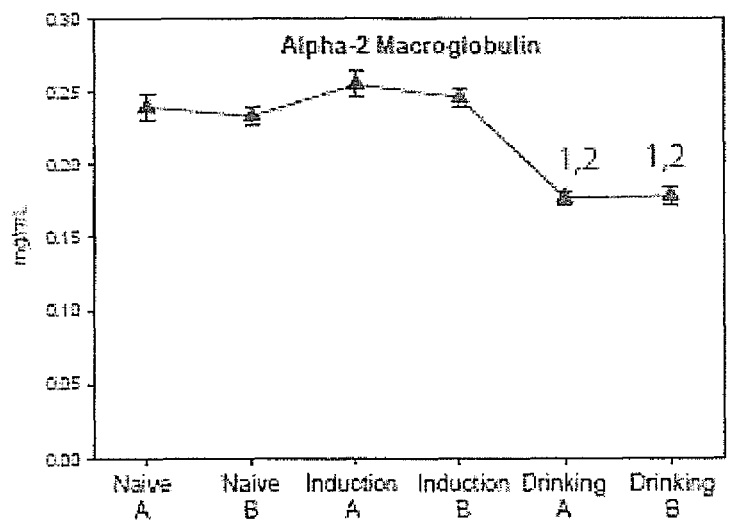
FIG. 4B is a graph showing alpha-2-macroglobulin plasma expression across drinking states.
Figure 4C:
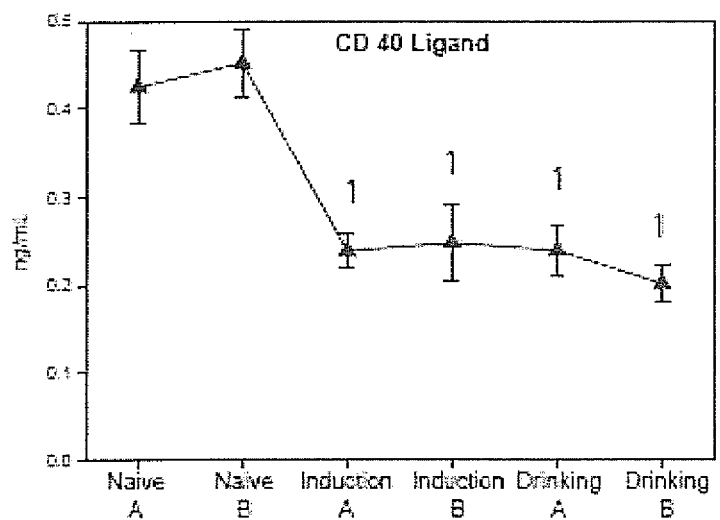
FIG. 4C is a graph showing CD 40 ligand plasma expression across drinking states.
Figure 4D:
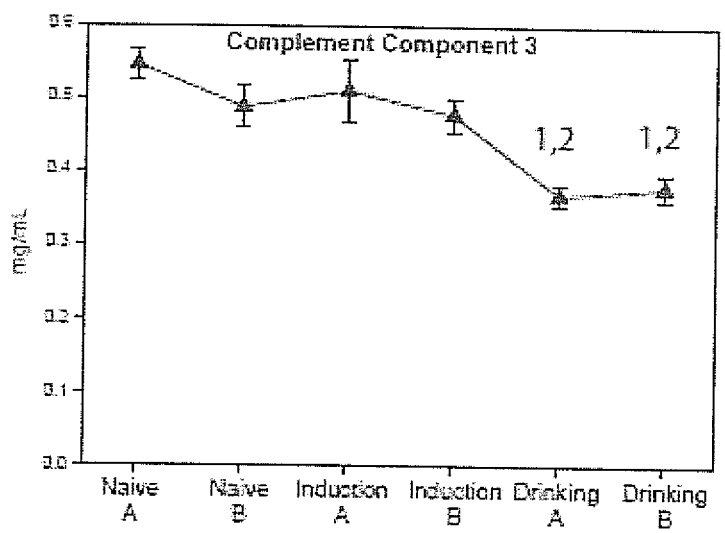
FIG. 4D is a graph showing complement component 3 plasma expression across drinking states.
Figure 4E:
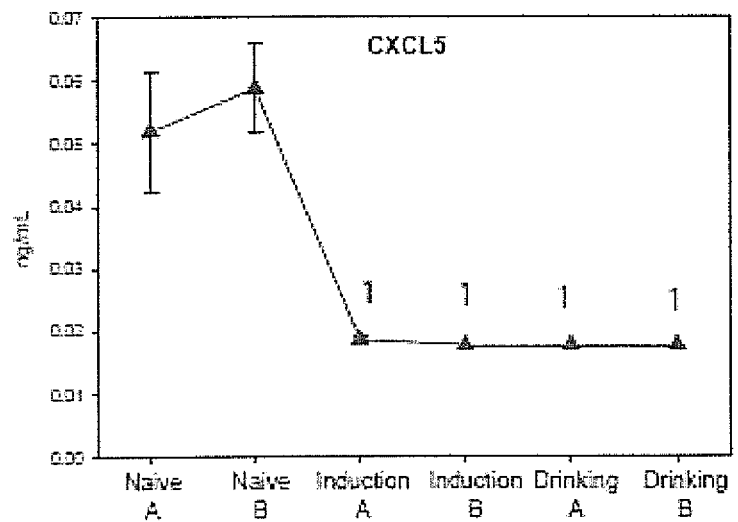
FIG. 4E is a graph showing CXCL5 plasma expression across drinking states.
Figure 4F:
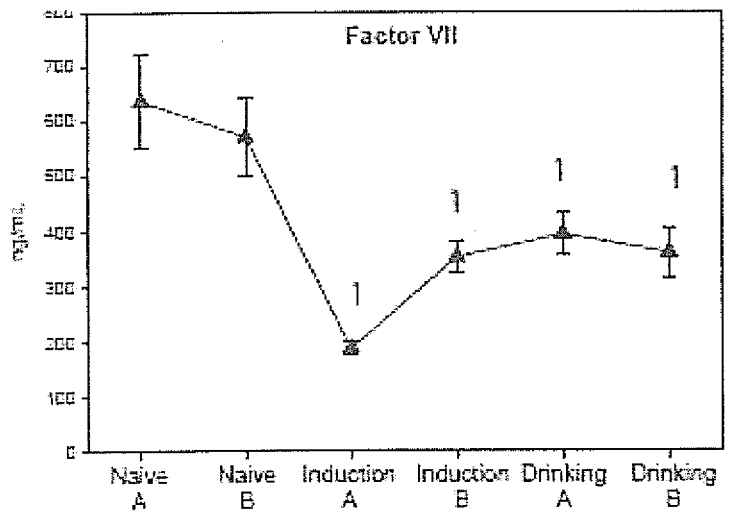
FIG. 4F is a graph showing Factor VII plasma expression across drinking states.
Figure 4G:
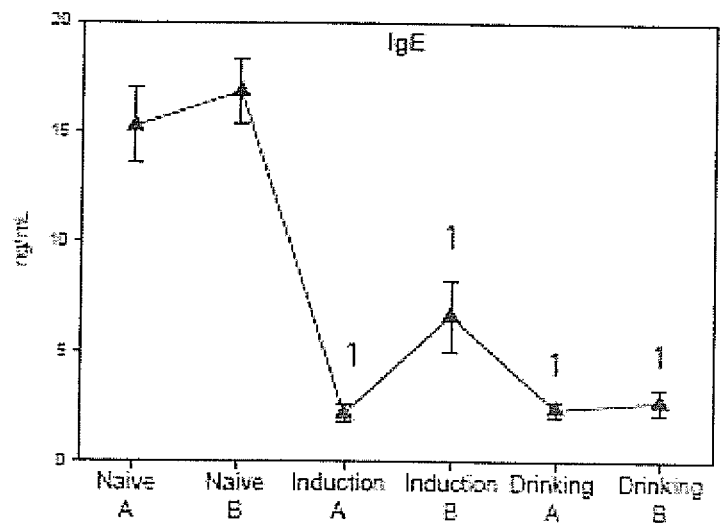
FIG. 4G is a graph showing IgE plasma expression across drinking states.
Figure 4H:
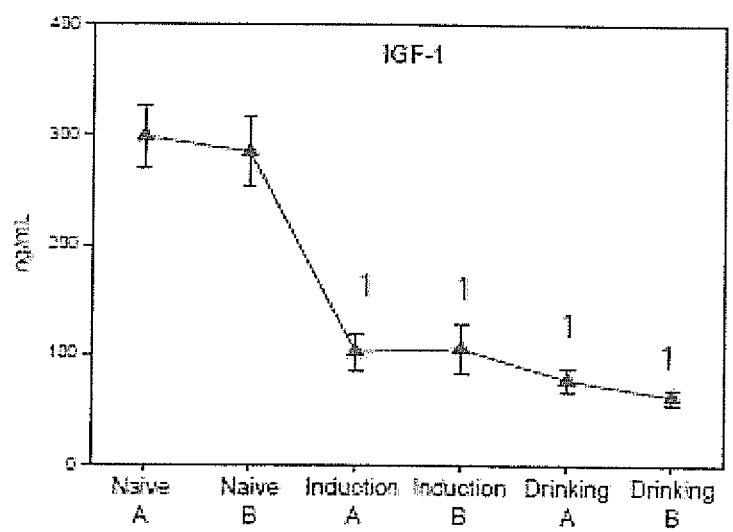
FIG. 4H is a graph showing IGF-1 plasma expression across drinking states.
Figure 4I:
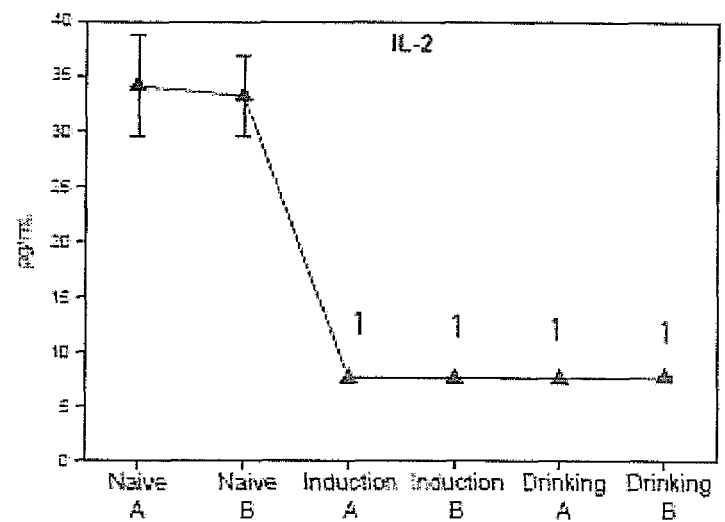
FIG. 4I is a graph showing IL-2 plasma expression across drinking states.
Figure 4J:
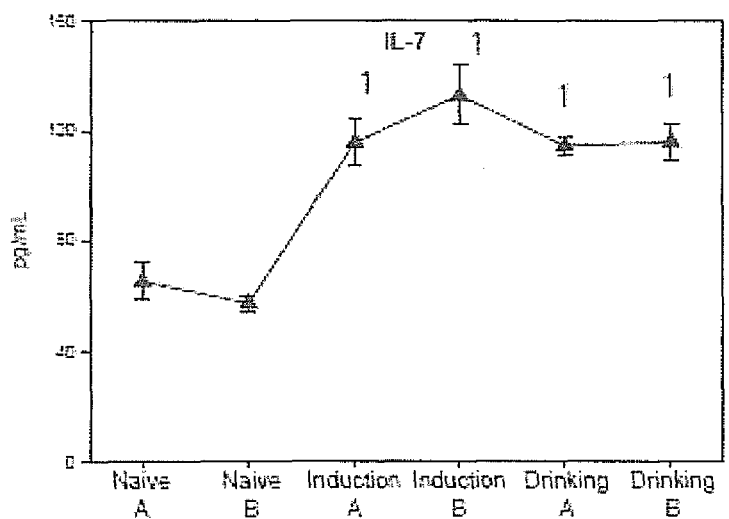
FIG. 4J is a graph showing IL-7 plasma expression across drinking states.
Figure 4K:
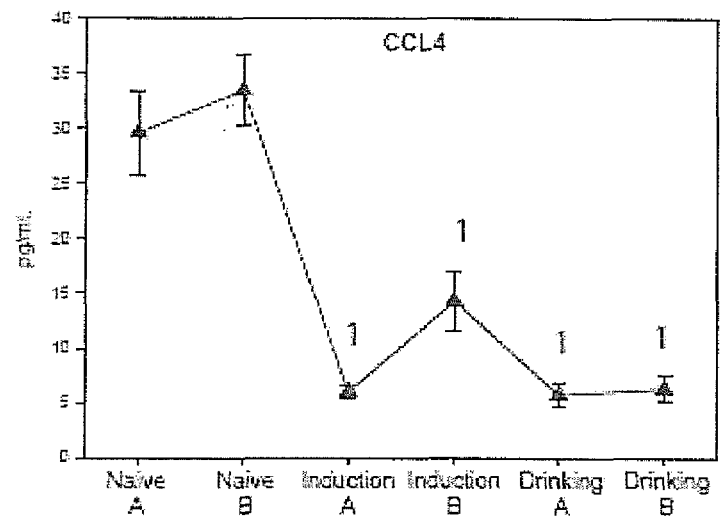
FIG. 4K is a graph showing CCL4 plasma expression across drinking states.
Figure 4L:
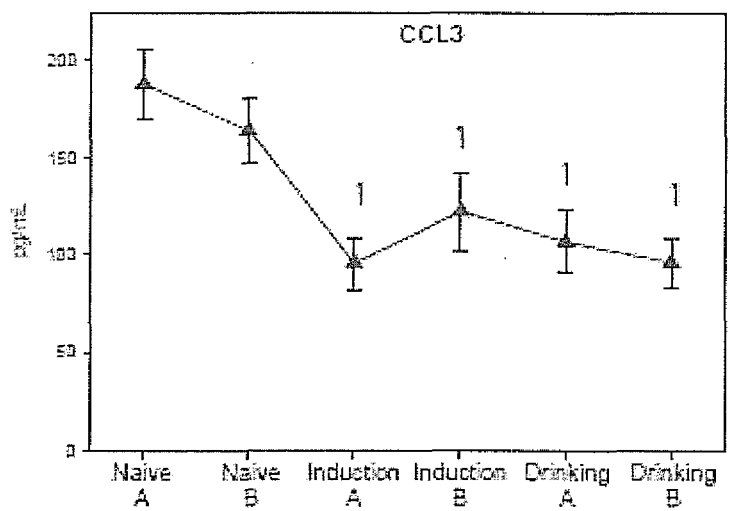
FIG. 4L is a graph showing CCL3 plasma expression across drinking states.
Figure 4M:
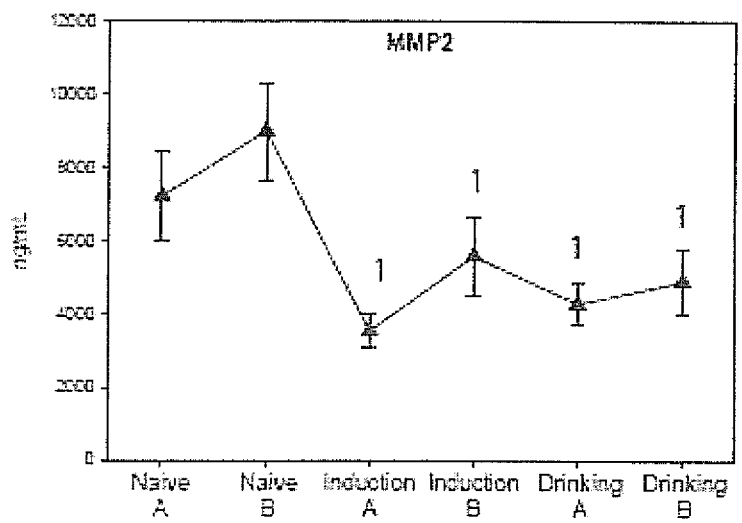
FIG. 4M is a graph showing MMP2 plasma expression across drinking states.
Figure 4N:
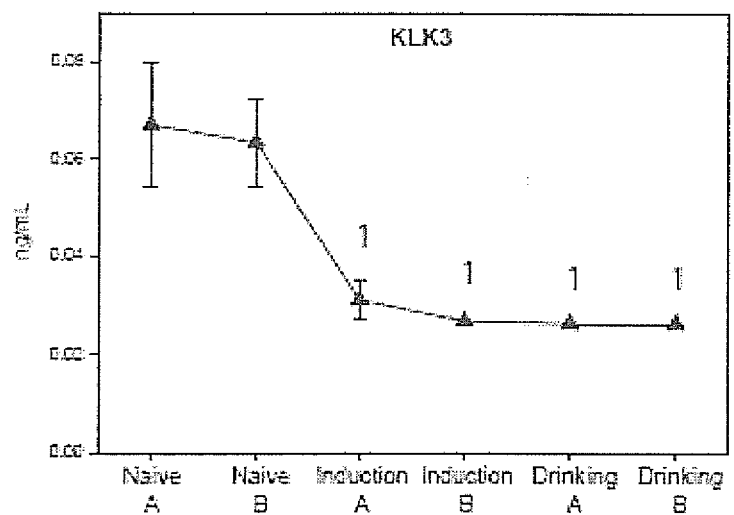
FIG. 4N is a graph showing KLK3 plasma expression across drinking states.
Figure 4O:
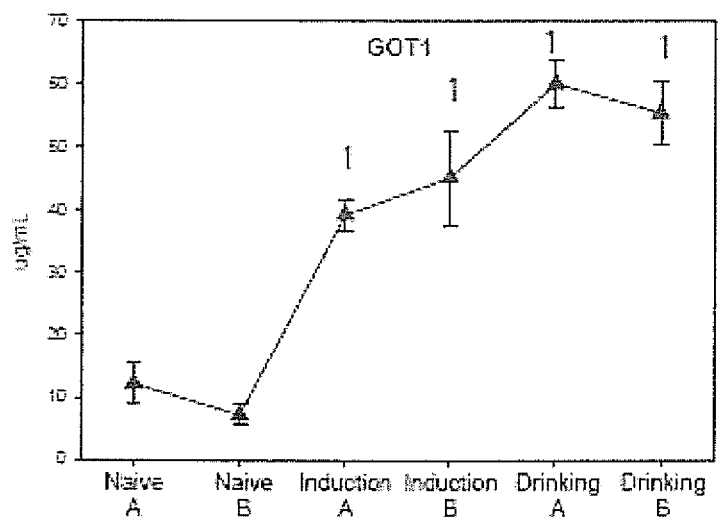
FIG. 4O is a graph showing GOT1 plasma expression across drinking states.
Figure 4P:
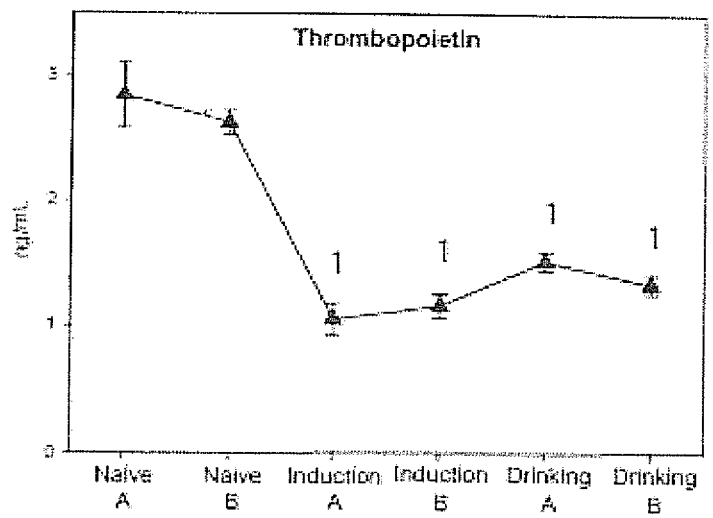
FIG. 4P is a graph showing Thrombopoietin plasma expression across drinking states.
Figure 4Q:
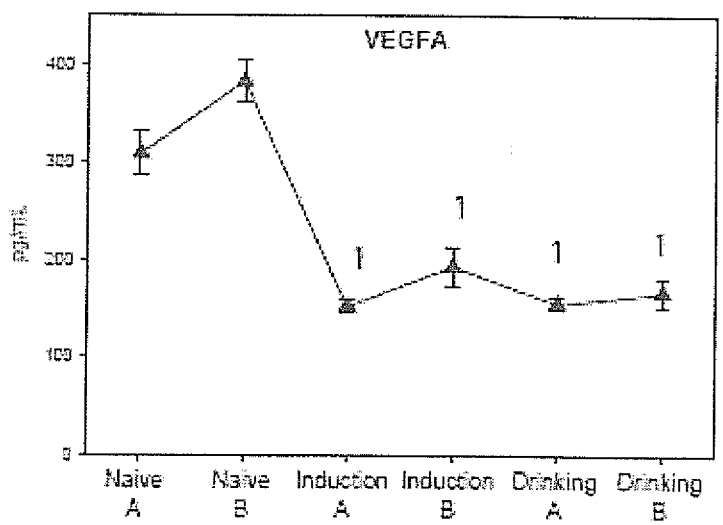
FIG. 4Q is a graph showing VEGFA plasma expression across drinking states.

Initial biomarker discovery is conducted by multiplex Luminex analysis of 90 known plasma cytokines, growth factors, and other proteins (Table III). Two independently collected samples (A and B) are analyzed for each of the three drinking states (Naïve, Induction, Drinking) (FIG. 1A) to identify the most consistently altered proteins. Sixty-one of the 90 proteins are present at detectable levels. Correlation of ethanol consumption with the level of protein concentration changes did not reveal significant associations. Proteins to be included in the biomarker panel are selected based on statistically-significant differences in protein abundance between both A and B samples in at least two of the three pair-wise drinking state comparisons (FIGS. 4A-Q). FIGS. 4A-Q are a set of graphs showing individual protein biomarker protein plasma expression across drinking states. One-Way ANOVA, Bonferroni multiple testing correction, 1, p<0.001 SNK post hoc versus Naive A & B; 2, p<0.001 SNK post hoc versus Induction A & B.

Figures 2B, 2C:
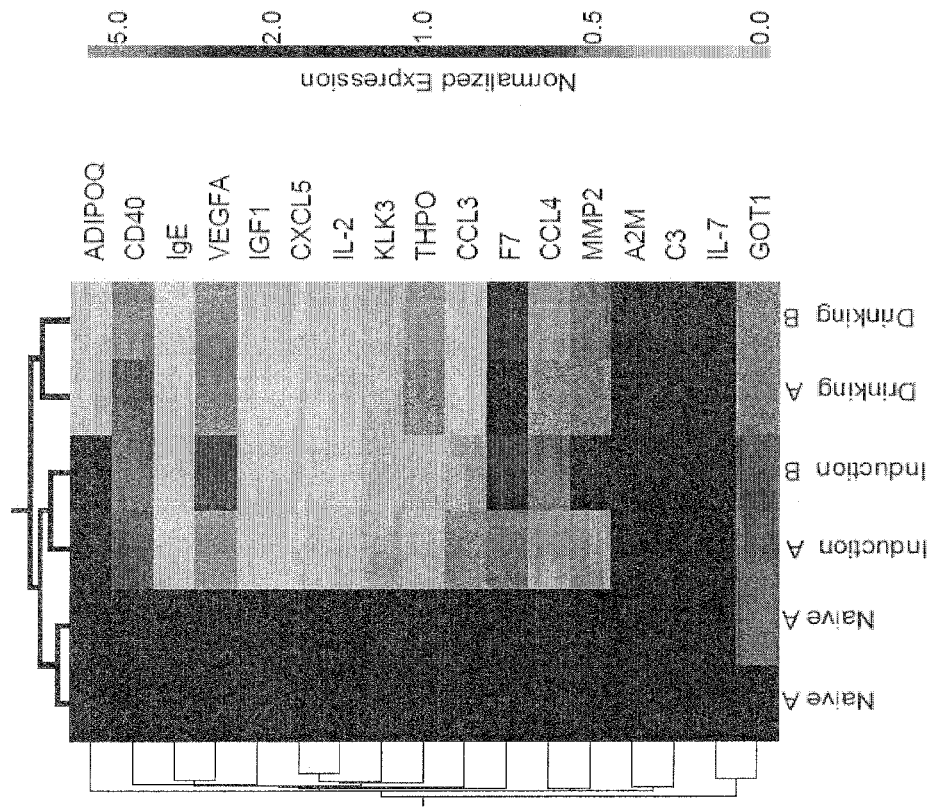
FIG. 2C is a "heatmap" showing normalized expression of selected proteins in nave subjects as well as after "Induction" of alcohol and in "Drinking" subjects.

The 17 proteins that met this criterion are tested for their classification accuracy using a Support Vector Machine (SVM) algorithm. Using a crossvalidation approach, alcohol abuse is correctly classified with 92% accuracy (Drinking vs. Naïve and Induction) (FIG. 2A) using a three protein biomarker set [adiponectin (ADIPOQ), alpha-2-macroglobulin (A2M), complement component 3 (C3)]. FIG. 2A is a diagram showing that using a three protein panel and Support Vector Machine (SVM) classification algorithm, alcohol abuse samples (Drinking) are correctly classified from non-alcohol abusing samples (Naïve and Induction) with 92% accuracy and 100% sensitivity. Alcohol use (Induction and Drinking samples) is correctly classified with 88% accuracy from non-alcohol using samples (Naïve) (FIG. 2B) using a 14 protein biomarker panel [(CD40, chemokine ligand 5 (CXCL5), Factor VII (F7), IgE, IGF1, interleukin 2 (IL2), interleukin 7 (IL7), chemokine (C-C motif) ligand 3 (CCL3), chemokine (C-C motif) ligand 4 (CCL4), matrix metallopeptidase 2 (MMP2), kallikrein-related peptidase 3 (KLK3), glutamic-oxaloacetic transaminase 1 (GOT1), thrombopoietin (THPO), vascular endothelial growth factor A (VEGFA)]. FIG. 2B is a diagram showing that using a fourteen protein panel and SVM classification algorithm, alcohol using samples (Induction and Drinking) were correctly classified from non-alcohol using samples (Naïve) with 88% accuracy and 95% sensitivity. The combined biomarker panel is presented in FIG. 2C. FIG. 2C is a Heatmap representation of the seventeen protein biomarker panel and clustering of the sample groups. Mean expression levels, normalized to a mean naïve level of 1, for each drinking state and time point were clustered by condition. Magnitudes of change are indicated by the intensity of the grayscale and are representative of the changes represented in FIGS. 4A-4Q. Independent samples from each drinking state clustered together.

Analysis using A samples as a Training Set and B samples as a Test Set, the accuracy of the alcohol abuse and alcohol use classifications are 87% and 97% respectively (FIG. 5). FIG. 5 is a diagram showing classification analysis using a training set/test set approach. Using A samples from each drinking state as the training set the B samples are classified using a support vector machine approach. Similar results are obtained from flipping of training and test sets. PPV—positive predictive value, NPV—negative predictive value. Reversal of the training and test sets returned similar results and use of an alternate algorithm (K-means nearest neighbor) results in similar accuracy.

Example 2

Non-Human Primates

Figure 6A:
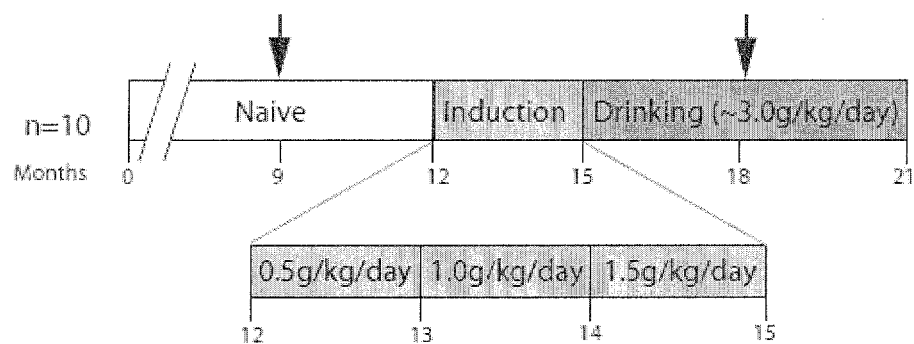
FIG. 6A is a diagram showing animal treatment paradigm and ethanol intakes indicating the time course of non-human primate alcohol self-administration and plasma sampling points.

Ten male cynomolgus monkeys (*macaca fascicularis*) are part of a 21-month experimental time line (FIG. 6A). For the first year (Naïve samples), monkeys aged 5-6 years (average weight 4.5 kg), are acclimated to the study environment and operant instrumentation, and trained to present their leg for venipuncture from the saphenous and/or femoral veins without the use of an anesthetic agent. Plasma samples are collected for endocrine tests, monitoring of blood alcohol levels, and for biomarker discovery and validation. Monkeys are induced to consume liquids under a schedule of food pellet deliveries (i.e., schedule-induced polydipsia as described in Falk, 1961, Science 133, 195-196), as described in Grant et al., 2008, Alcoholism: Clinical and Experimental Research 32, 1824-1838. Induction conditions did not require food deprivation, just scheduling access, and are not associated with weight loss. Ethanol is presented in the form of 4% w/v ethanol (unflavored). Following one month of 0.5 g/kg/day ethanol, the animals are escalated to drink 1.0 g/kg/day for 30 consecutive days, and finally, 1.5 g/kg/day for 30 consecutive days. Animals are then given unlimited access (22 hours per day) to ethanol and water for six months (Drinking samples) as described in Grant et al., 2008, Alcoholism: Clinical and Experimental Research 32, 1824-1838; and Vivian et al., 2001, Alcoholism: Clinical and Experimental Research 25, 1087-1097). Plasma samples from Naïve and Drinking time points are collected for proteomic discovery and validation experiments.

Figure 6B:
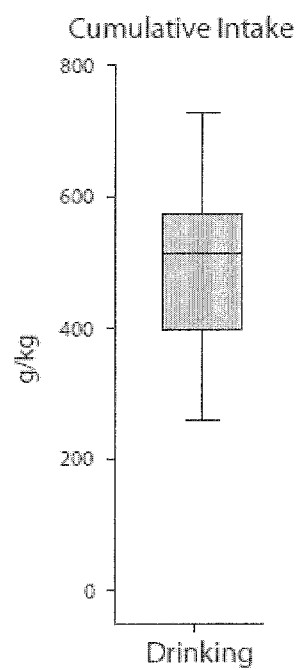
FIG. 6B is a graph showing that the cumulative self-administered intake in the previous six months at the Drinking time point averaged 495 g/kg.
Figure 6C:
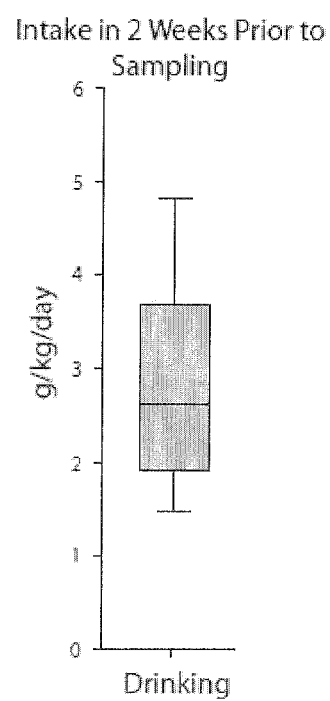
FIG. 6C is a graph showing the average daily intake of 2.89 g/kg/day in the two weeks prior to collection of the Drinking sample.

For non-human primate within-subject biomarker target discovery and confirmation experiments, alcohol Naïve samples and samples collected after 3 months of excessive alcohol consumption (Drinking) are used (FIG. 6A). At collection of Drinking samples, monkeys had 22/hr/day access to ethanol. Cumulative intake over the experimental timeline at the time of plasma collection averaged 495 g/kg (FIG. 6*b*). In the two weeks prior to sampling, average daily ethanol consumption is 2.89 g/kg (FIG. 6*c*)—a value equivalent to approximately 12 drink equivalents per day. FIG. 6A is a diagram showing animal treatment paradigm and ethanol intakes indicating the time course of non-human primate alcohol self-administration and plasma sampling points. Following one year of acclimatization (naïve period), monkeys are induced to drinking under schedule-induced polydipsia. During the induction phase, monkeys drink up to 0.5, 1.0, and 1.5 mg/kg of alcohol a day for a month at each dose. Following the three month induction period, monkeys are allowed free access to alcohol. Plasma samples are collected at times indicated by the arrows. FIG. 6B is a graph showing the cumulative self-administered intake in the previous six months (three months of induction and three months of open access) at the Drinking time point averaged 495 g/kg. FIG. 6C is a graph showing that in the two weeks prior to collection of the Drinking sample, the average daily intake was 2.89 g/kg/day.

Hu-14 Protein Depletion

Abundant proteins are depleted from non-human primate samples to improve the sensitivity of proteomic experiments as described in Freeman et al., 2006, Proteomics 6, 3109-3113. In this example, an affinity column designed to capture the 14 most abundant plasma proteins (albumin, IgG, antitrypsin, IgA, transferrin, haptoglobin, fibrinogen, alpha2-macroglobulin, alpha 1-acid glycoprotein, IgM, apolipoprotein AI, apolipoprotein AII, complement C3, and transthyretin) (Hu-14, Agilent) is used as described in Zolotarjova et al., 2008, Journal of Chromatography A 1189, 332-338. To ensure required protein yields, samples are depleted in duplicate. Plasma samples are passed through a 0.22 µm spin filter and 40 µL of plasma sample is injected onto a 4.6 mm internal diameter Hu-14 column at room temperature (Aktaprime Plus, GE Healthcare). The flow-through fraction is collected and, after the addition of high salt buffer, the bound proteins are collected. Fractions are monitored in-line by UV absorbance. Samples are concentrated before further use with a 5 kDa MW cut-off spin concentrator (Vivascience).

Figure 7A:
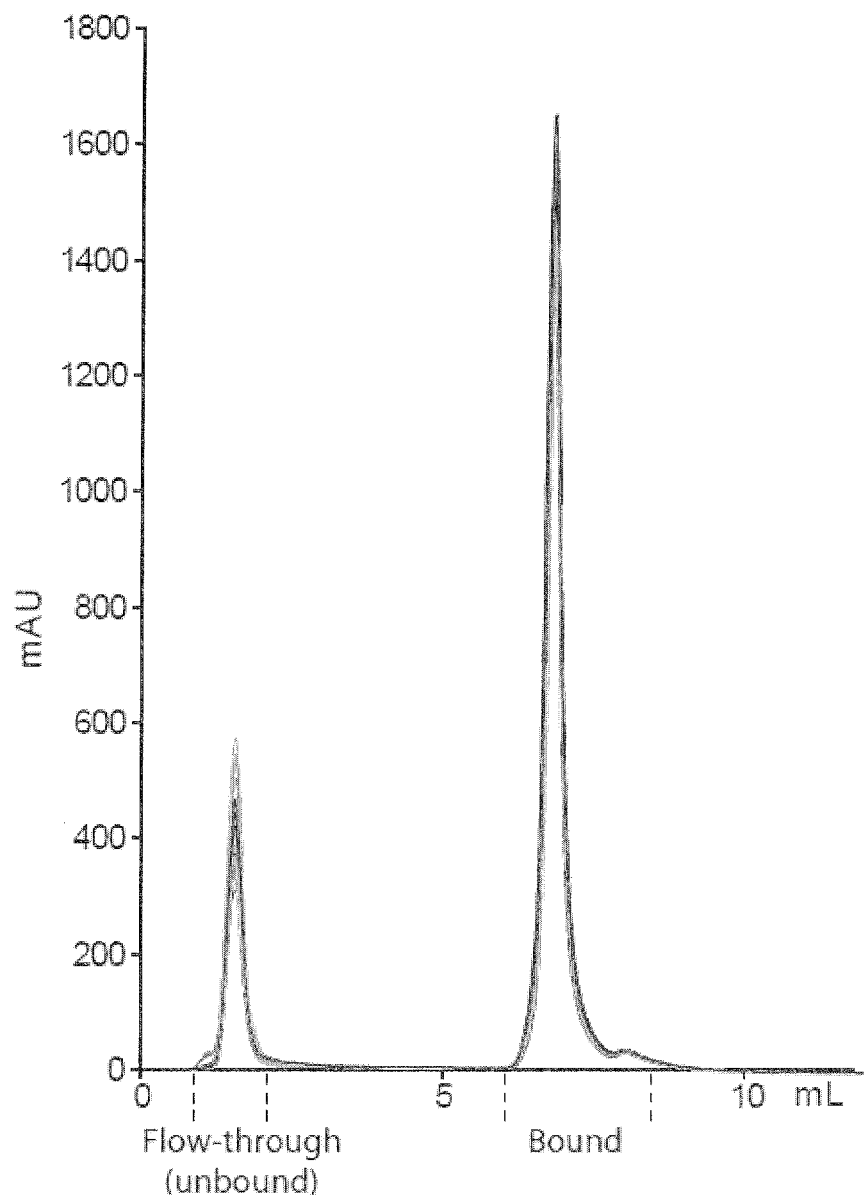
FIG. 7A is a graph showing a co-plot of chromatograms from separate depletions of abundant plasma proteins from plasma.
Figure 7B:
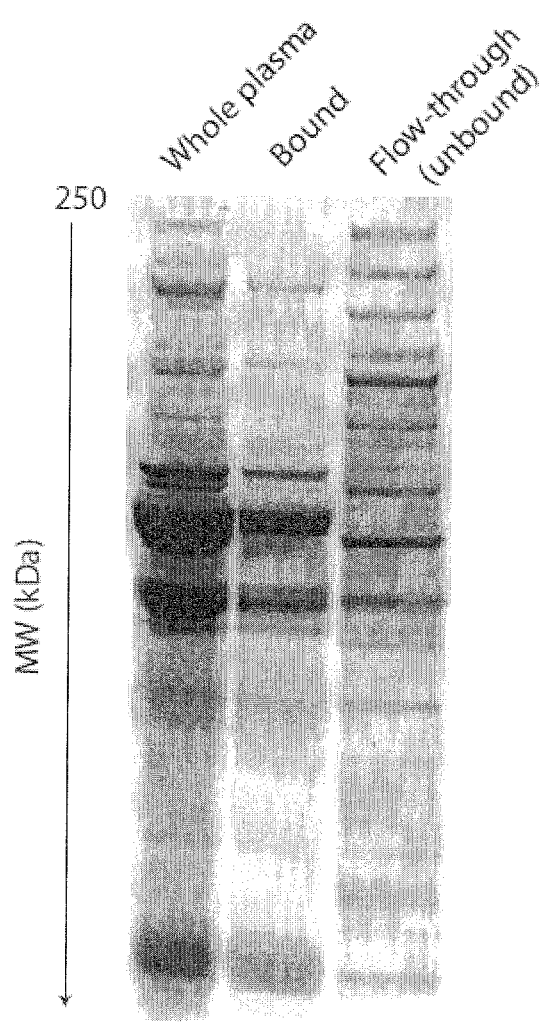
FIG. 7B is an image of proteins from whole plasma, bound fraction and flow through separated on a polyacrylamide gel visualized with Deep Purple stain for total protein.
Figure 7C:
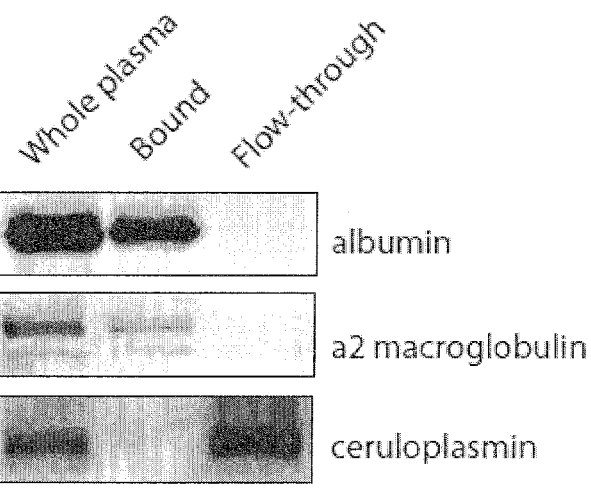
FIG. 7C is an image of immunoblots showing specificity of depletion of abundant plasma proteins.
Figure 7D:
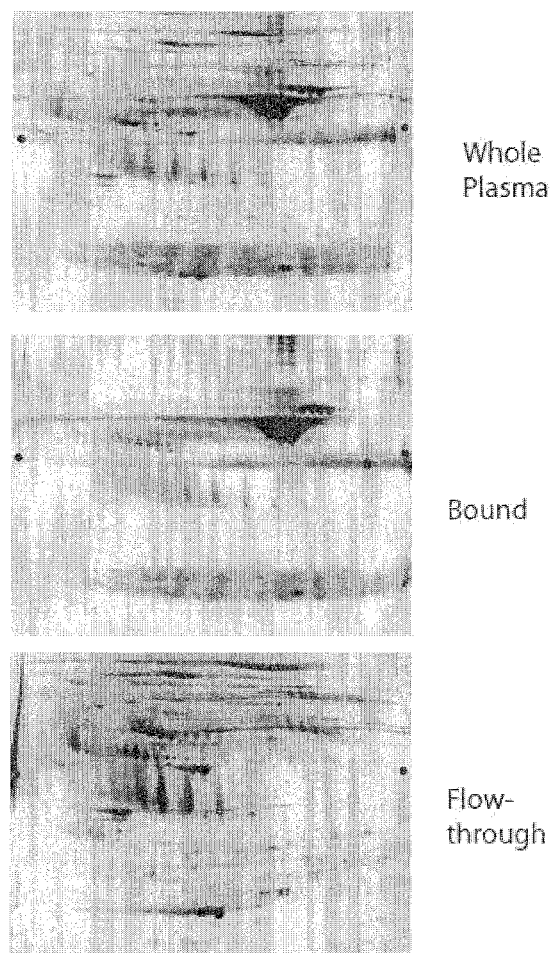
FIG. 7D is an image of the pattern of proteins evident after 2-D electrophoresis after depletion of abundant plasma proteins.

To characterize the consistency and specificity of the 14 protein affinity depletion column used in this study with non-human primate samples, a series of quality control experiments are performed. In-line monitoring of plasma depletion demonstrated consistent flow-through and protein binding patterns across all 40 depletions (FIG. 7a). Quantitation of the flow through and bound fractions demonstrated 95% of plasma protein bound to the column with 5% of the protein found in the flow-through. No differences in flow-through fraction yields are evident between Naïve and Drinking samples. Quality control assessment of equal amounts of protein from undepleted whole plasma, bound fraction, and flow through separated by SDS-PAGE demonstrated an expected change in the pattern of proteins observed with the most prominent bands in the whole plasma present in the bound fraction but not in the flow-through (FIG. 7b). Immunoblotting for proteins to be removed by the depletion column (albumin and α2 macroglobulin) and for a negative control that should not be removed by the column (ceruloplasmin) revealed depletion of intended proteins, but no non-specific depletion (FIG. 7c). Two-dimensional electrophoresis of equal protein masses of whole plasma, bound fraction, and flow-through visualized the removal of abundant proteins and the detection of additional proteins apparent in the flow-through that are masked in the whole plasma (FIG. 7d). FIG. 7A is a graph illustrating the reproducibility of plasma depletions. Chromatograms from forty independent depletions are co-plotted onto the same graph. Minimal run-to-run differences are observed. Each of the forty depletions is co-plotted as an independent line in FIG. 7A and due to the consistency of the chromatography appears as a single line. The flow-through fraction is collected for further analysis and the bound fraction is eluted by addition of high salt buffer. FIG. 7B illustrates results where equal amounts of protein from whole plasma, bound fraction and flow through were separated on a 10-14% gradient SDS polyacrylamide gel and visualized with Deep Purple protein stain. After affinity depletion of high abundance proteins, a number of protein bands that are not apparent in whole plasma are revealed. FIG. 7C is a set of images that show that specificity of the affinity depletion is confirmed by immunoblotting for proteins that should be bound to the column (albumin, a2-macroglobulin) and proteins that should not be bound to the column (ceruloplasmin). FIG. 7D is a set of images of 2D gels showing the pattern of proteins evident after 2-D electrophoresis separation of equal amounts of proteins demonstrates that removal of high abundance proteins (in bound fraction) allows for illumination of protein spots previously obscured or at levels below detection (in flow-through fraction).

2D-DIGE

Quantitative two-dimensional in-gel electrophoresis (2D-DIGE) is performed as detailedin (Umstead et al., 2010, Pediatric Research 67, 641-649; and VanGuilder et al., 2010, Journal of Neurochemistry 113, 1577-1588. Protein from depleted plasma is purified of contaminants by precipitation (2-D Cleanup, GE Healthcare), resuspended in sample buffer (Tris-HCl, 2M thiourea, 7M urea, 2.0% CHAPS, 1.0% ASB-14, pH 8.5), and quantified by 2D-Quant protein assay (GE Healthcare). Individual samples (n=10/group) are adjusted to pH 8.0-9.0 and 50 µg of each sample is labeled with appropriate cyanine (Cy) dyes (GE Healthcare). A normalization pool containing equal protein from each sample, labeled with $Cy_2$, is included on each gel to standardize quantitation. Unlabeled normalization, pool protein (250 µg) is used for pre-parative/picking gels for mass spectrometry (MS) identification of proteins. Labeled samples are combined (one Naïve control, one Drinking, and one normalization pool aliquot per analytical gel) for a total of ten gels, mixed with equal volumes of 2× sample buffer (7M urea, 2M thiourea, 2.0% CHAPS, 2.0% pH 3-10NL pharmalyte, 1.0% DeStreak reagent), and brought to a volume of 450 µL with DeStreak rehydration buffer containing 0.5% 3-10 NL pharmalyte (GE Healthcare). Samples are resolved by isoelectric point on 24-cm, pH 3-10 nonlinear strip gels (GE Healthcare). Strip gels are then equilibrated to SDS and reduced and alkylated. SDS-PAGE second dimension separation is performed on 10-14% polyacrylamide gradient gels poured using an automated pump system (a2DE optimizer, NextGen Sciences, Ann Arbor Mich.). Picking gels are fixed and post-stained with Deep Purple (GE Healthcare). Gels are imaged (Typhoon 9410 scanner, GE Healthcare) with identical, optimized PMT voltages used for all gels for each channel. Automated analysis of gel images is performed using DeCycler 6.5 software (GE Healthcare) to detect spots and calculate relative expression values. Only spots confidently matched across at least 8 of 10 quantitative gels are included in statistical analyses. Differential expression is determined by two-tailed paired t-test with false discovery rate correction (p<0.05).

MALDI-ToF/ToF mass spectrometry

MALDI-ToF/ToF mass spectrometry is performed as described in VanGuilder et al., 2010, Journal of Neurochemistry 113, 1577-1588. Spots are excised using a robotic Ettan Spot Picker (GE Healthcare), trypsin digested, and desalted (ZipTip, Millipore, Bedford, Mass.). Samples are spotted onto a MALDI target followed by 0.8 µL of ACH-cinnamic acid. MS Measurements are taken in the positive ion mode between 800-4000 m/z with a signal-to-noise filter of 10, mass exclusion tolerance of 0.2Da, and a peak density filter of 50 peaks per 200Da (Applied Biosystems 4800). The 10 most intense ions with a minimum signal to noise of 75 that are not included on an exclusion list containing trypsin autolysis, matrix, and tryptic peptides of human keratin are subjected to MS/MS. MS/MS is performed without collision-induced decay in a mass range from 60Da to 20Da below the precursor mass with a fragment tolerance of 0.2Da for +1 charged ions. Protein identifications are made using GPS explorer v3.6 with Mascot v2.0.00 and the primate taxonomy of the NCBI database downloaded on Feb. 16, 2008 (107,758 entries). Identifications required a confidence interval of greater than 99%. When multiple isoforms of a protein are identified in the same MALDI target spot, the isoform with the highest confidence interval is reported which either: 1) has an identified peptide exclusive to that isoform; or 2) has the theoretical molecular weight and pI that matched the gel spot location.

LC-MS/MS Mass Spectrometry

Tryptic peptides extracted from ten gel plugs, matching to the ten largest magnitude and statistically-significant changes, are analyzed by on-line nano LC/MS/MS and ThermoFisher LTQ Orbitrap XL (NextGen Sciences, Ann Arbor, Mich.) as described in VanGuilder et al., 2010, Journal of Neurochemistry 113, 1577-1588. This additional analysis is performed to maximize identification success for these protein spots of interest. 30 µL of tryptic peptide solution is loaded on a 75 mm C12 vented column at a flow-rate of 10 µL/min and eluted at 300 mL/min with the following one hour gradient (time in minutes:% elution buffer): 0.1 min:3%, 30 min:23%, 38 min:32%, 42 min:50%, 44 min:95%, 47 min: 95%, 47.5 min:1.0%, 55 min: 1.0%. MS/MS ion searches are conducted with the following specifications: monoisotopic mass values; peptide mass accuracy of ±2.0Da; fragment mass tolerance of ±0.5Da; one missed trypsin cleavage; fixed carbamidomethyl (C); variable modifications: oxidation (M), acetyl (N-term), pyro-glu (N-term-Q). MASCOT-generated data files are processed using the Scaffold algorithm. Parameters for LTQ-based protein identification required a minimum of three peptide matches per protein with minimum probabilities of 95% at the protein level and >50% at the corresponding peptide level.

Results of 2D-DIGE and Mass Spectrometry

Figure 8A:
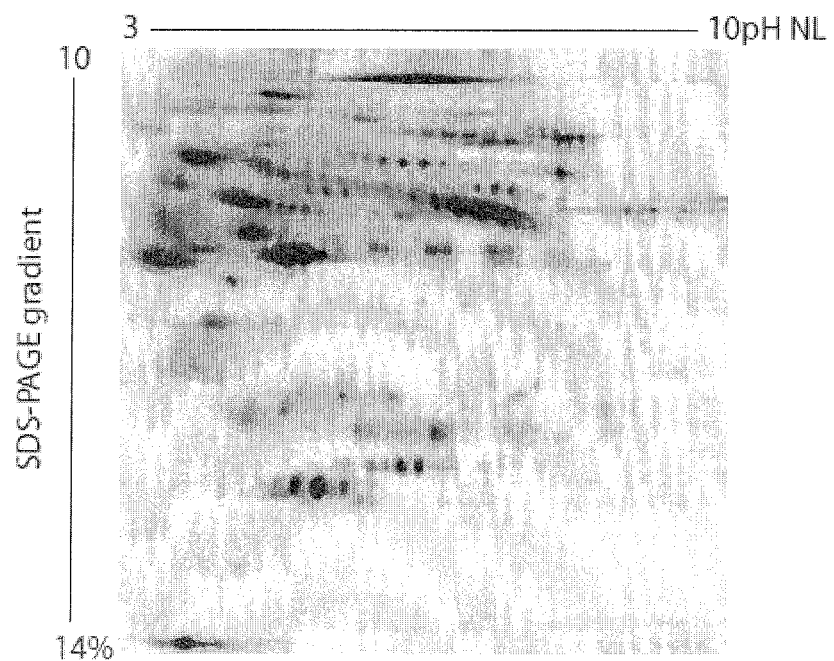
FIG. 8A is an image showing 2D-DIGE of abundant protein depleted plasma.
Figure 8B:
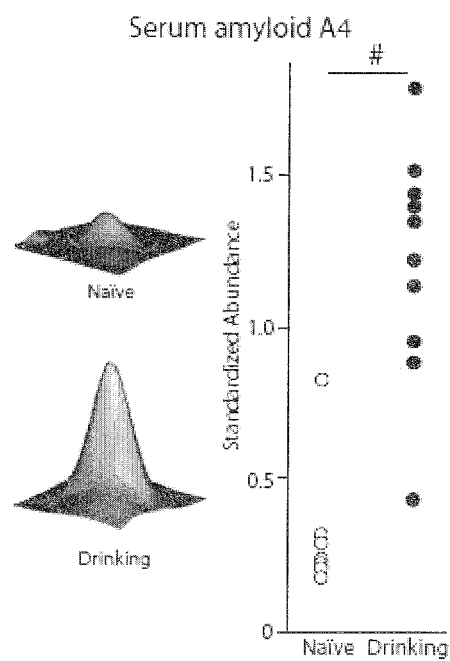
FIG. 8B is a graph showing 2D-DIGE results indicating Serum Amyloid A4 is increased in Drinking Samples.
Figure 9A:
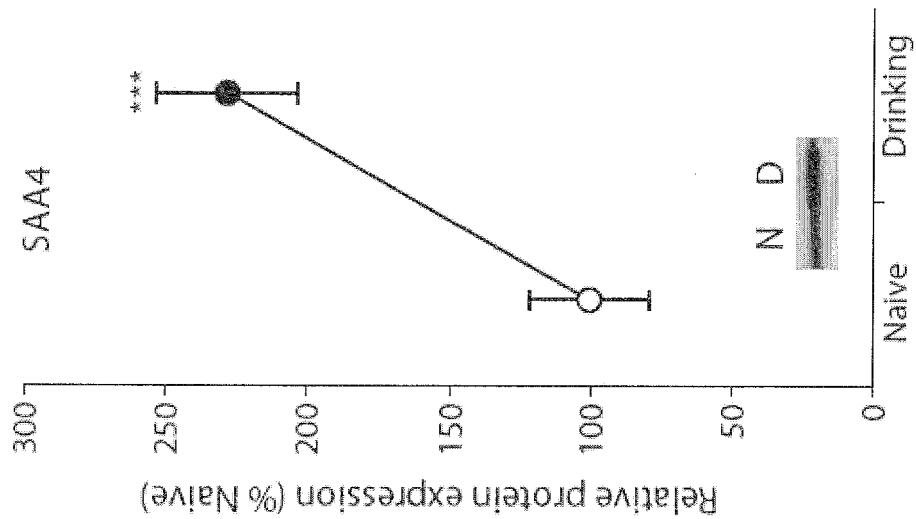
FIG. 9A is a graph showing relative expression of SAA4 in naive vs. Drinking subjects.
Figure 8C:
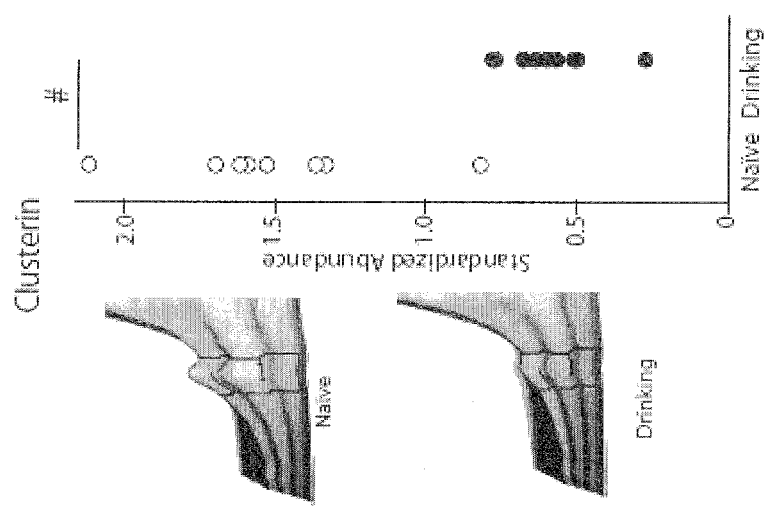
FIG. 8C is a graph showing 2D-DIGE results indicating clusterin is decreased in Drinking Samples.
Figure 9C:
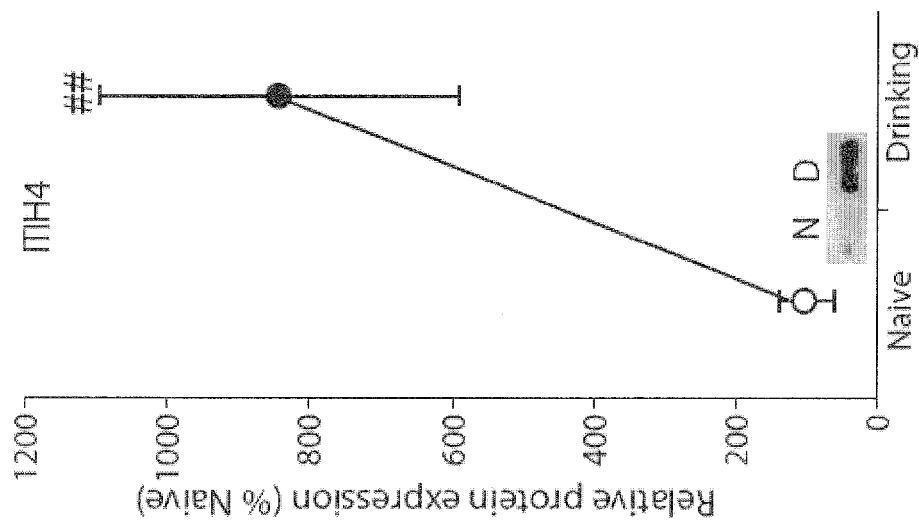
FIG. 9C is a graph showing relative expression of ITIH4 in naive vs. Drinking subjects.
Figure 9B:
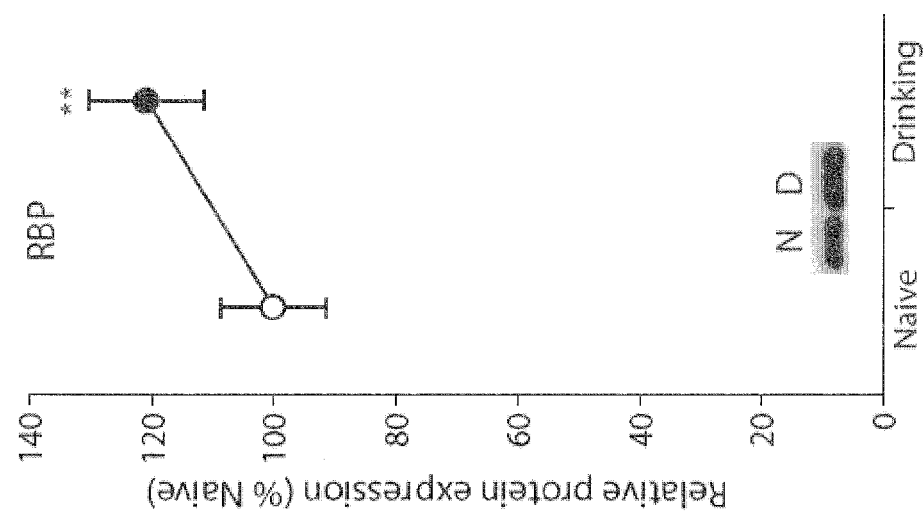
FIG. 9B is a graph showing relative expression of RBP in naive vs. Drinking subjects.
Figures 9D, 9E:
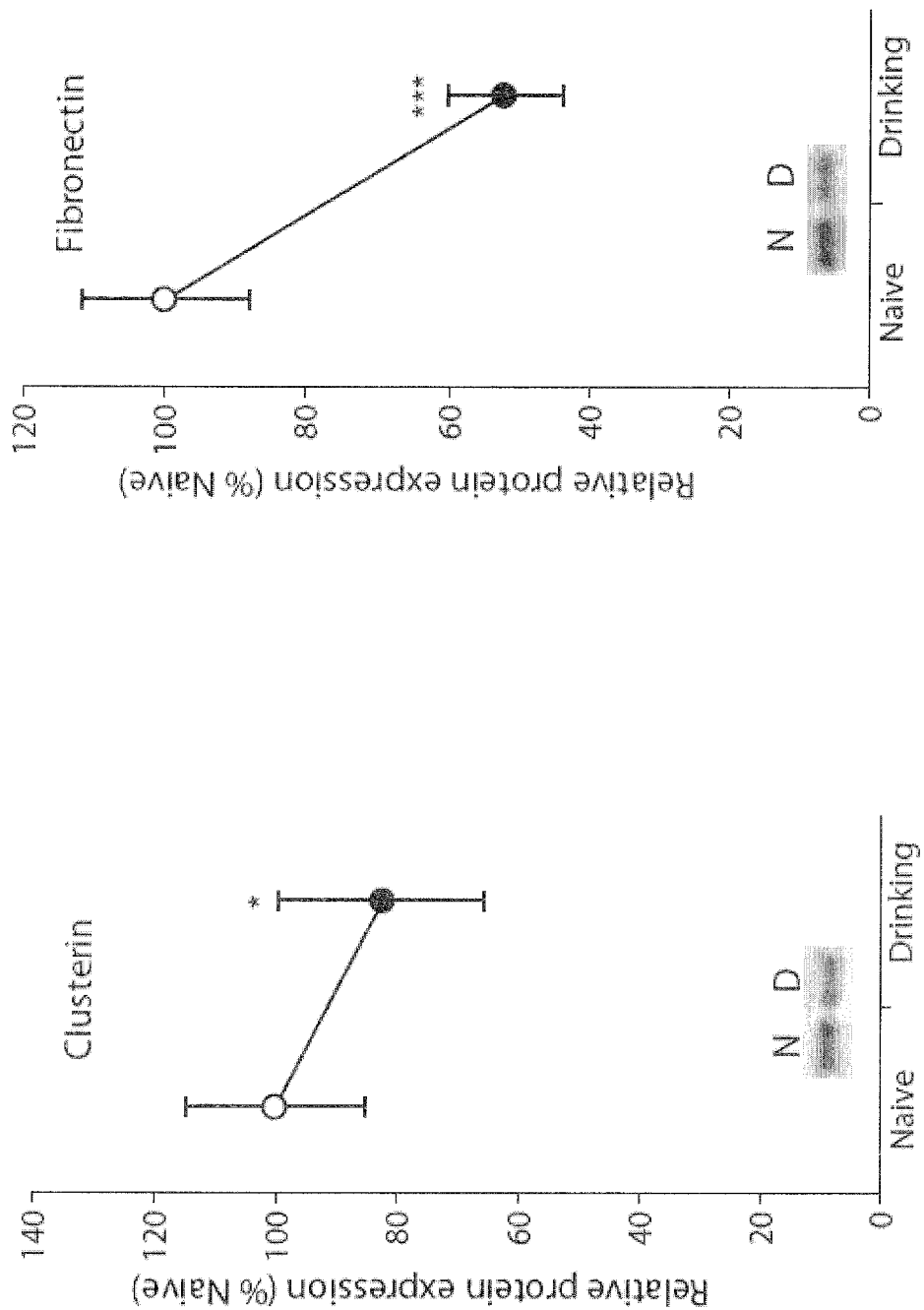
FIG. 9D is a graph showing relative expression of clusterin in naive vs. Drinking subjects.
FIG. 9E is a graph showing relative expression of fibronectin in naive vs. Drinking subjects.

Labeled proteins separated by isoelectric point and molecular weight produced consistent spot patterns on analytical and picking gels. A total of 722 protein spots are matched across 8 or more of the analytical gels. Paired, two-tailed t-tests determined that 190 protein spots (~25% of total matched spots) are differentially regulated in drinking vs. naïve subjects (paired t-test with false discovery rate multiple testing correction; $p<0.05$, 1.15-fold change cutoff). 106 protein spots are upregulated by 1.15- to 10-fold with drinking, while 84 protein spots are downregulated by 1.15- to 17-fold. 199 protein spots, representing both ethanol-regulated and stably-expressed species, that are matched to a picking gel are identified with >99% confidence by either MALDI- or LTQ-mass spectrometry (Supplementary Table S1). 46 differentially-regulated plasma proteins are confidently identified exemplified by clusterin, inter-alpha inhibitor H4, serum amyloid A4 in FIG. 8A-C. FIG. 8A shows an example of 2D-DIGE results. Abundant protein depleted plasma is subjected to 2D-DIGE quantitative analysis to identify proteins with differing abundance between Naïve and Drinking group. A total of 190 spots are significantly different between groups, and two examples are provided. FIG. 8B is a graph showing increased levels of Serum Amyloid A4 observed ($p<0.001$) in Drinking samples. A 3D image of representative spot volumes is provided to the left. FIG. 8C is a graph showing decreased levels of Clusterin are evident in Drinking samples as compared to Naïve control samples ($p<0.001$).

As described for examination of abundant protein depletion in monkey plasma samples using an anti-human antigen affinity column in Freeman et al., 2006, Proteomics 6, 3109-3113, depletion efficacy is very high but not 100% as evidenced by identification of apoliprotein A1, C3, and alpha 1-acid glycoprotein by mass spectrometric analysis likely due to amino acid sequence differences in these proteins between human and monkey.

Human Subjects

To assess biomarker targets in human samples, cross-sectional samples are collected under Institutional Review Board approved protocol with informed consent from medically healthy (including screening for Hepatitis C) control subjects and patients who met DSM-IV diagnostic criteria for alcohol dependence as described in American Psychiatric Association, 2000 Diagnostic and Statistical Manual of Mental Disorders DSM-IV-TR, Washington, D.C. Both groups may have met diagnostic criteria for nicotine dependence, but they are excluded if structured diagnostic interview as described in American Psychiatric Association, 2000 Diagnostic and Statistical Manual of Mental Disorders DSM-IV-TR, Washington, D.C.; First et al., 2010 Structured Clinical Interview for DSM-IV-TR Axis I Disorders (SCID-I/NP). New York: Biometrics Research Department, New York State Psychiatric Institute; Spitzer and Williams, 2002, Structured Clinical Interview for the DSM-IV Axis 1Disorders-Patient Edition (SCID-I/P, Version 2.0). New York: Biometrics Research Department, New York State Psychiatric Institute, found evidence of Axis I psychiatric diagnoses or substance abuse dependencies. Both groups also are free of psychotropic substances for at least four weeks prior to study entry (excluding nicotine, ethanol, and caffeine). Clinical history is supported by urine toxicology screening. Time-line-follow-back is used to estimate the quantity of alcohol consumed in the 30 days prior to sample collection as described in Sobell and Sobell, 1992, Timeline follow-back: a technique for assessing self-reported alcohol consumption. In: Litten R, Allen J (Eds.), Measuring Alcohol Consumption. (pp. 41-72) New York: Humana Press.

Immunoblotting

Whole, unmanipulated plasma samples from monkeys and human subjects are used to eliminate the potential of any artifacts introduced by affinity depletion. Paired samples from one monkey are not included in immunoblot experiments as the samples for this animal and time point are exhausted in the 2D-DIGE study. Samples are diluted 1:10 with protein lysis buffer (100 mM NaCl, 20 mM HEPES, 1 mM EDTA, 1 mM dithiothreitol, 1.0% Tween20, 1 mM $Na_3VO_4$, 1 Complete Mini EDTA-free Protease Inhibitor Cocktail Tablet for every 10 mL lysis buffer), and filtered with 0.22 µm spin filters to remove particulate matter. Protein concentrations are determined by BCA protein assay (Pierce), and all samples are adjusted to equal protein concentration with additional lysis buffer. Equal amounts of protein from all samples are resolved on Criterion 4-20% acrylamide gradient Tris-HCl gels (Bio-Rad) and transferred to HyBond PVDF membranes (GE Healthcare). After blocking in 5% fat free milk (mouse primary antibodies) or 3% BSA (goat primary antibody) in phosphate-buffered saline with 1% Tween-20, membranes are probed with primary antibodies (mouse anti-RBP, Santa Cruz [#sc46688]; goat anti-ITIH4, Santa Cruz [#sc21987]; mouse anti-albumin, Sigma [#A6684]; mouse anti-fibronectin, Sigma [#F0916]; mouse anti-SAA4, Sigma [#sab1400251]; mouse anti-clusterin, Millipore [#05-354]) diluted in new blocking buffer, by overnight incubation at 4° C. After washing, blots are incubated with species-appropriate HRP-conjugated secondary antibodies, developed with ECL substrate (GE Healthcare), imaged on x-ray film, and digitized at a resolution of 600 dpi for subsequent quantitation. Images are quantified using ImageQuant TL 2007 software with rolling ball background subtraction.

Immunoblot Confirmation

To confirm protein expression changes with alcohol intake, selected proteins with the largest magnitude differences between Naïve and Drinking time points and identified by 2D-DIGE/MS are quantitated in whole monkey plasma by immunoblotting. Whole plasma is used in confirmation experiments to eliminate any quantitation bias introduced by plasma depletion and to provide a matrix (whole plasma) most similar to that which would be used clinically. Undepleted naïve and drinking samples are probed for SAA4, RBP4, ITIH4, clusterin, and fibronectin, with albumin included as an unchanged loading control. Total protein staining (Deep Purple and Ponceau) of gels also demonstrated highly consistent protein quantitation and loading (FIG. 11). FIGS. 11A-E show immunoblot protein standardization. Immunoblot data for both non-human primate and human samples are normalized to total protein to correct for any potential differences in protein loading. Deep-Purple total protein staining demonstrates the consistency of protein loading between individual samples and experimental groups.

In agreement with the proteomic quantitation, samples collected from drinking animals contained significantly more SAA4 (229±25.0% of naïve, 418)=−11.11, $p<0.001$), RBP4 (120±9.3% of naïve, t(18)=−3.93, $p<0.01$), and ITIH4 (844±251.7% of naïve, z(18)=2.55, $p<0.01$) compared to their paired ethanol-naïve samples (FIG. 9). Decreased expression of clusterin (82±16.9% of naïve, t(16)=2.55, $p<0.05$) and fibronectin (52±8.2% of naïve, t(18)=5.13, $p<0.001$) is also observed by immunoblotting (FIG. 9). FIGS. 9A-E are graphs showing orthogonal confirmation of 2D-DIGE findings. To confirm biomarker targets identified in the 2D-DIGE analysis, specific immunoblotting is performed using undepleted plasma samples. Significantly higher protein concentrations of SAA4, RBP, and ITIH4 are evident while statistically significant decreases in clusterin and fibronectin abundance are observed. *$p<0.05$, $p<0.01$, *$p<0.001$, paired student's t-test, two-tailed, ##$p<0.01$, Wilcoxon signed rank test, n=9/group.

Consistent changes are observed between paired Naïve and Drinking samples with some overlap between conditions (FIG. 12). FIGS. 12A-E are dot plots of non-human primate immunoblot data. Specific immunoblotting is performed using undepleted plasma samples from Naïve and Drinking non-human primate samples. Paired samples are indicated by lines.

Human Subject Validation

Figure 10B:
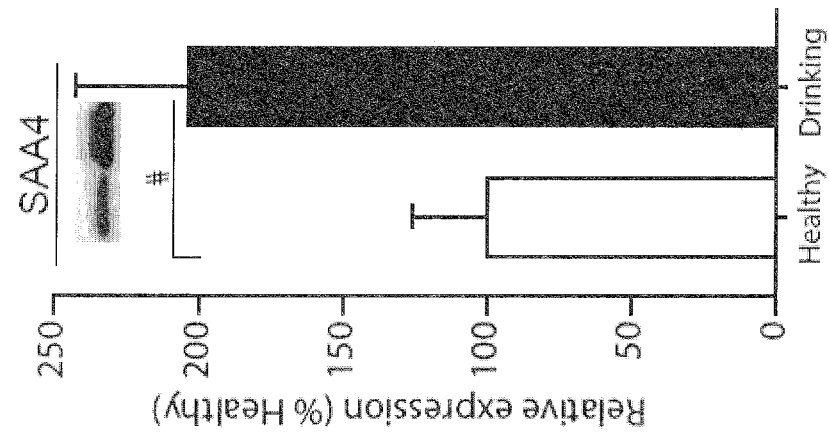
FIG. 10B is a graph showing relative expression of SAA4 in Healthy vs. Drinking subjects.
Figure 10A:
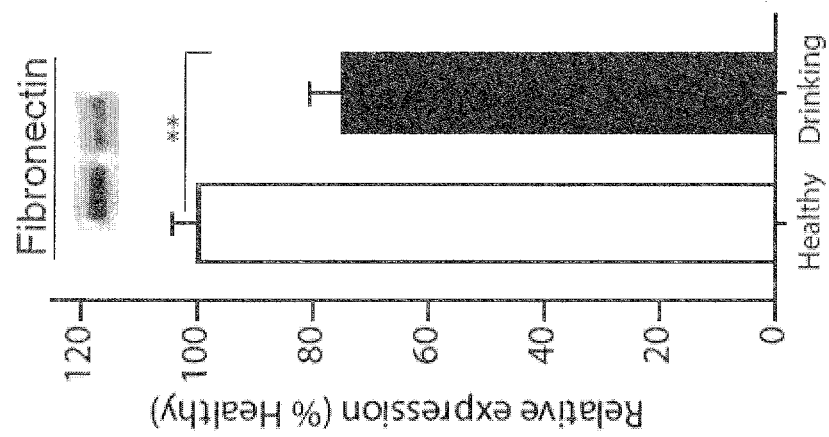
FIG. 10A is a graph showing relative expression of fibronectin in Healthy vs. Drinking subjects.
Figure 10C:
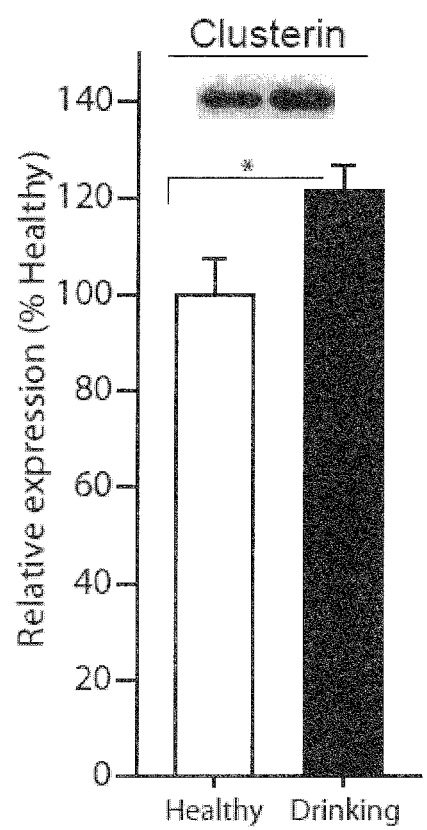
FIG. 10C is a graph showing relative expression of clusterin in Healthy vs. Drinking subjects.
Figure 11A:
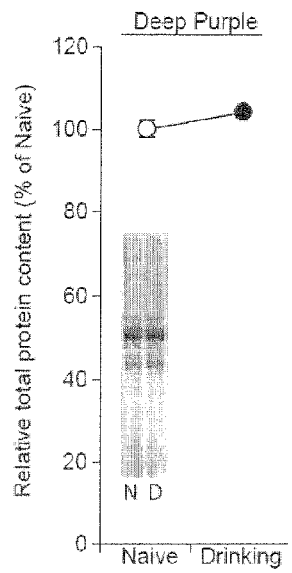
FIG. 11A is a graph showing immunoblot protein standardization for non-human primate subject samples from naive and Drinking subjects using Deep Purple total protein staining; the inset shows a reproduced image of a gel stained to show total protein.
Figure 11B:
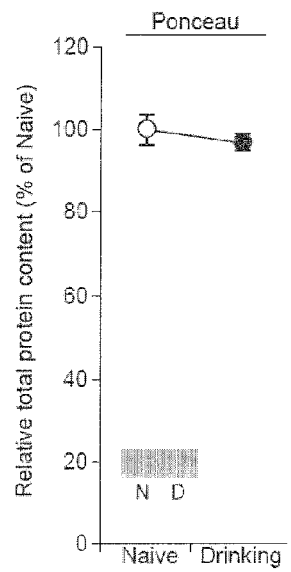
FIG. 11B is a graph showing immunoblot protein standardization for non-human primate subject samples from naive and Drinking subjects using Ponceau total protein staining; the inset shows a reproduced image of a gel stained to show total protein.
Figure 11C:
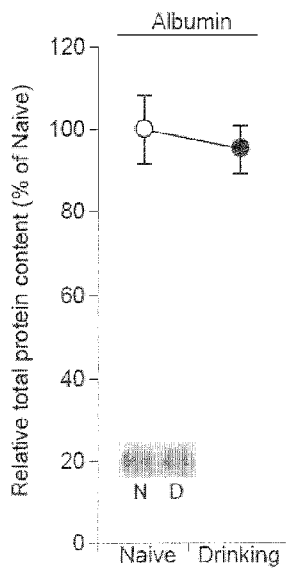
FIG. 11C is a graph showing immunoblot protein standardization for non-human primate subject samples from naive and Drinking subjects using albumin staining; the inset shows a reproduced image of a gel stained to show albumin.
Figure 11D:
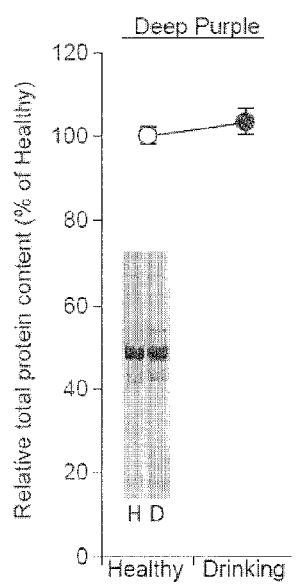
FIG. 11D is a graph showing immunoblot protein standardization for human subject samples from naive and Drinking subjects using Deep Purple total protein staining; the inset shows a reproduced image of a gel stained to show total protein.
Figure 11E:
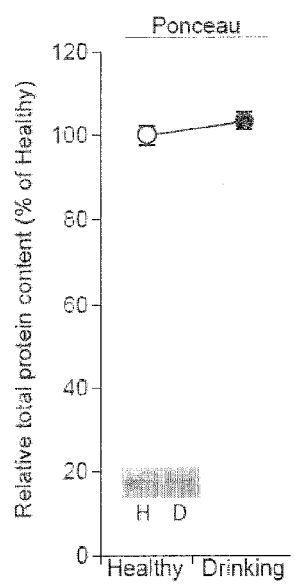
FIG. 11E is a graph showing immunoblot protein standardization for human subject samples from naive and Drinking subjects using Ponceau total protein staining; the inset shows a reproduced image of a gel stained to show total protein.
Figure 11F:
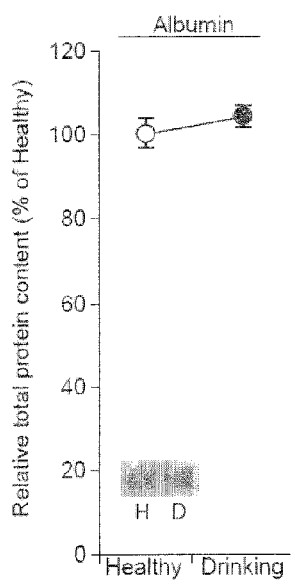
FIG. 11F is a graph showing immunoblot protein standardization for human subject samples from naive and Drinking subjects using albumin staining; the inset shows a reproduced image of a gel stained to show albumin.
Figure 12B:
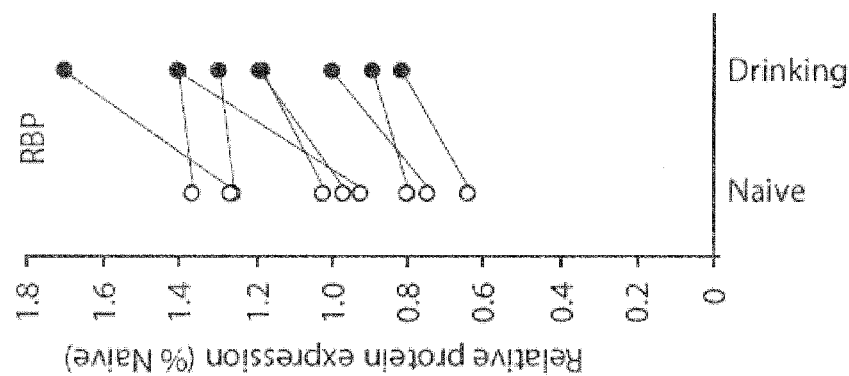
FIG. 12B is a graph showing a dot plot of non-human primate subject RBP immunoblot data for undepleted samples from Healthy and Drinking subjects, wherein paired samples are indicated by lines.
Figure 12A:
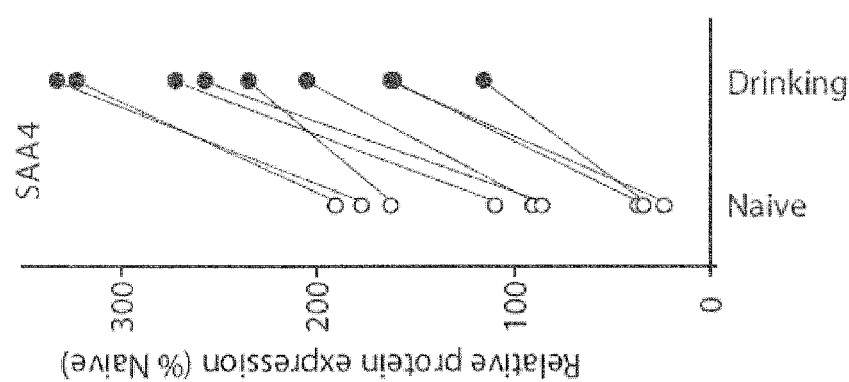
FIG. 12A is a graph showing a dot plot of non-human primate subject SAA4 immunoblot data for undepleted samples from Healthy and Drinking subjects, wherein paired samples are indicated by lines.
Figure 12D:
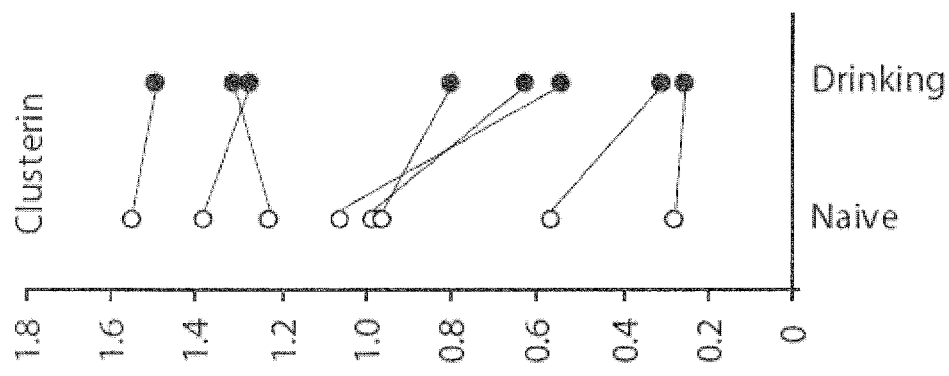
FIG. 12D is a graph showing a dot plot of non-human primate subject clusterin immunoblot data for undepleted samples from Healthy and Drinking subjects, wherein paired samples are indicated by lines.
Figure 12C:
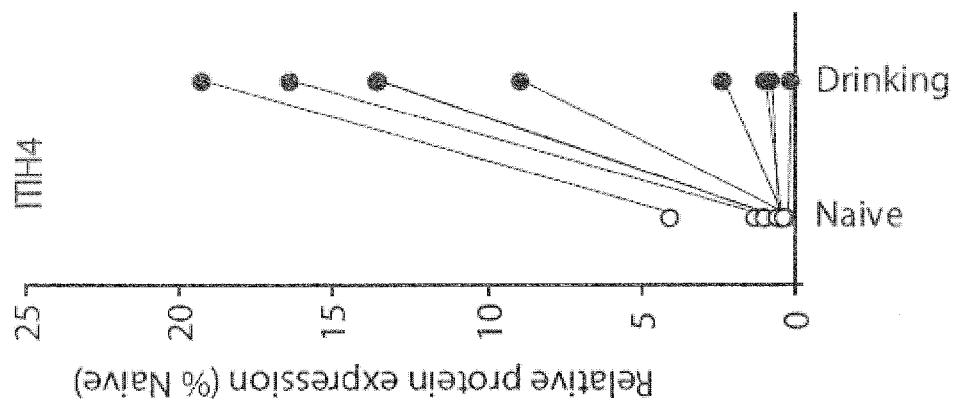
FIG. 12C is a graph showing a dot plot of non-human primate subject ITIH4 immunoblot data for undepleted samples from Healthy and Drinking subjects, wherein paired samples are indicated by lines.

Plasma samples from healthy and heavily drinking human patients are immunoblotted for protein targets identified in monkey samples. Plasma samples from eight alcohol dependent men (average age 41±7.5 years) and seven healthy male subjects (average age 35±9.8 years) are collected. In the month prior to sample collection, alcohol abusing subjects averaged 402±216 standard drinks consumed, as estimated by time-line-follow-back. Healthy subjects reported 4±4 standard drinks consumed in the previous month. Decreased fibronectin (75±5.7% of healthy, t(15)=3.42, $p<0.01$) and increased SAA4 (204±38.4% of naïve, U(15)=10, $p<0.05$) are confirmed in humans (FIG. 10). FIGS. 10A-C are graphs showing results of assessment of biomarkers fibronectin, SAA4 and clusterin in human subjects. To translate the findings of the differential plasma protein abundance in the non-human primate to humans, biomarker targets were assessed by immunoblotting in alcoholics and healthy controls. *$p<0.05$, **$p<0.01$, student's t-test, two-tailed, # $p<0.05$ Mann-Whitney rank sum test n=7-8/group.

Clusterin levels in alcohol abusing patients are 121±5.2% of healthy controls, t(15)=−2.35, $p<0.05$). Despite the significant differences between group means, some overlap in protein abundance is observed between Healthy and Drinking individuals (FIG. 13).

Figure 13A:
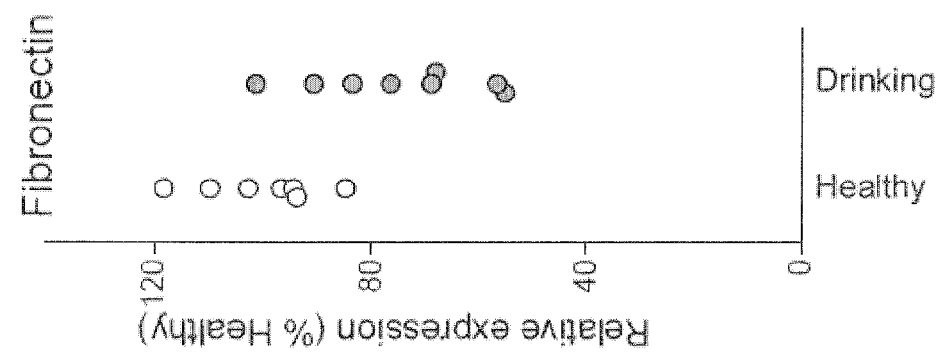
FIG. 13A is a graph showing a dot plot of human subject fibronectin immunoblot data for undepleted samples from Healthy and Drinking subjects.
Figure 12E:
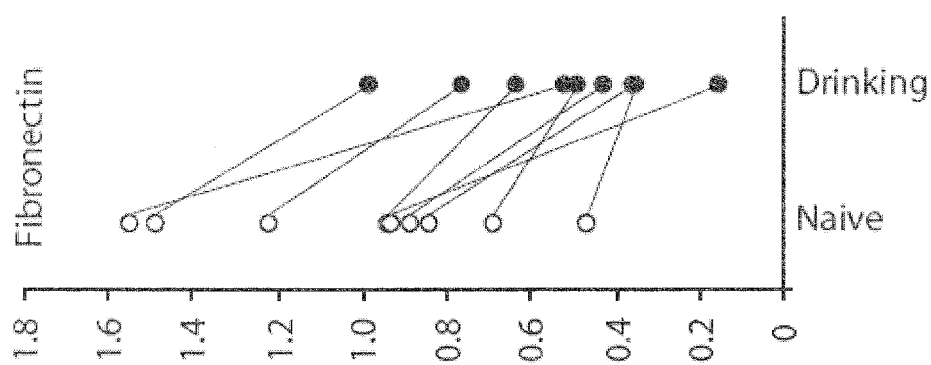
FIG. 12E is a graph showing a dot plot of non-human primate subject fibronectin immunoblot data for undepleted samples from Healthy and Drinking subjects, wherein paired samples are indicated by lines.
Figure 13C:
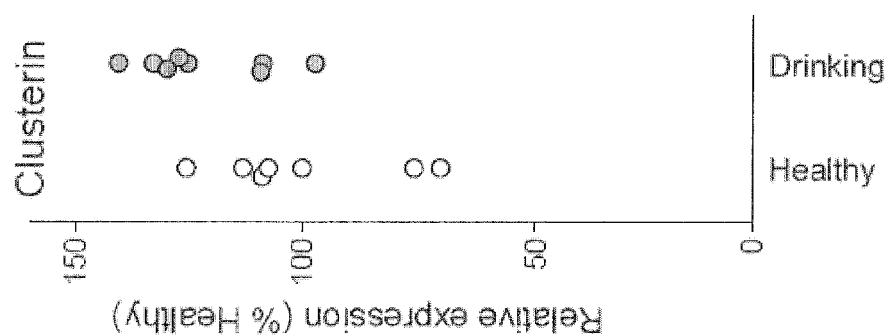
FIG. 13C is a graph showing a dot plot of human subject clusterin immunoblot data for undepleted samples from Healthy and Drinking subjects.
Figure 13B:
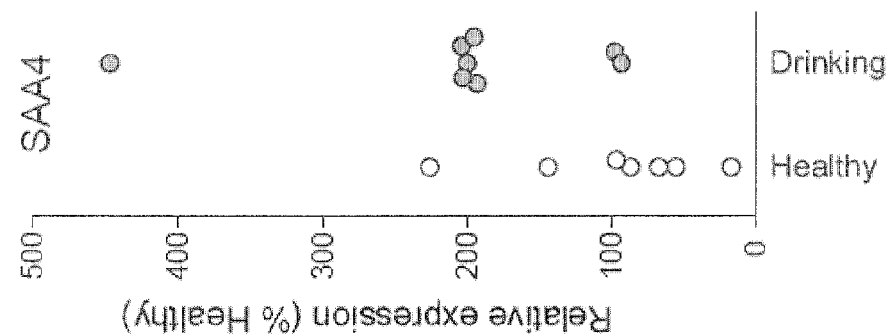
FIG. 13B is a graph showing a dot plot of human subject SAA4 immunoblot data for undepleted samples from Healthy and Drinking subjects.

FIGS. 13A-13C are dot plots of human subject immunoblot data. Specific immunoblotting is performed using undepleted plasma samples from Healthy and Drinking subjects. No differences in ITIH4 and RBP4 protein abundance are observed in human subjects.

Statistics

Immunoblotting data from longitudinal non-human primate samples are analyzed with a paired two-tailed t-test, or a Wilcoxon signed rank test for non-normally distributed data. Human subject samples are analyzed by unpaired two-tailed t-test, or a Mann-Whitney rank sum test for non-normally distributed data for cross-sectional human samples ($\alpha<0.05$).

Plasma samples from healthy and heavily drinking human patients are immunoblotted to assay for A1BG, A2M, ADIPQ, APCS1, APCS2, APOAI, APOC3, C3, C4a, C9, CALCA, CCL3, CCL4, CD40, CLU, CSF2, CXCL5, EGF, F3, F7, FABP3, FN1, GOT1, HRG, IgE, IGF1, IL12p70, IL18, IL2, IL7, KITLG, KLK3, MMP2, SAA4, SERPINF1, THPO, VCAM1 and/or VEGFA to obtain results similar to those found in non-human primate samples.

FIGS. 2A, 2B, 2C, 4A-Q, 9A-E, 10A-C, 12 and 13 and Tables I, II, III and V show results identifying A1BG, A2M, ADIPQ, APCS1, APCS2, APOAI, APOC3, C3, C4a, C9, CALCA, CCL3, CCL4, CD40, CLU, CSF2, CXCL5, EGF, F3, F7, FABP3, FN1, GOT1, HRG, IgE, IGF1, IL12p70, IL18, IL2, IL7, ITIH4, KITLG, KLK3, MMP2, RBP4, SAA4, SERPINF1, THPO, VCAM1 and VEGFA as biomarkers of non-consumption, moderate consumption or high consumption.

Table IV shows tissues-of-origin for biomarker proteins. The indicated proteins originate from a number of different organ systems and some proteins may come from multiple organ systems. This table was generated with information in the Ingenuity Pathway Analysis system (Ingenuity Systems, Redwood City, Calif.).

TABLE I

| Name | SwissProt | Symbol | p value | Drinking/Naïve | Level in Moderate or High Alcohol Consumer compared to non-drinker |
|---|---|---|---|---|---|
| Adiponectin | Q15848 | ADIPQ | # | 0.42 | decreased |
| Alpha-2 Macroglobulin | P01023 | A2M | # | 0.75 | decreased |
| Apolipoprotein A1 | P02647 | APOAI | * | 1.3 | increased |
| Apolipoprotein CIII | P02656 | APOC3 | * | 0.98 | decreased |
| Calcitonin | P01258 | CALCA | # | 0.33 | decreased |
| CD40 | Q6P2H9 | CD40 | # | 0.5 | decreased |
| Complement 3 | P01024 | C3 | # | 0.72 | decreased |
| EGF | P04141 | EGF | * | 0.11 | decreased |
| ENA-78 | P42830 | CXCL5 | ** | 0.32 | decreased |
| Factor VII | P08709 | F7 | # | 0.65 | decreased |
| Fatty Acid Binding Protein | P05413 | FABP3 | * | 0.47 | decreased |
| GM-CSF | | CSF2 | * | 1.76 | increased |
| IgE | | IgE | # | 0.16 | decreased |
| IGF-1 | P01343 | IGF1 | # | 0.24 | decreased |
| IL-12p70 | P29460 | IL12p70 | ** | 0.57 | decreased |
| IL-18 | | IL18 | # | 0.53 | decreased |
| IL-2 | P01585 | IL2 | # | 0.23 | decreased |
| IL-7 | P13232 | IL7 | # | 1.88 | increased |
| MIP-1alpha | P10147 | CCL3 | # | 0.19 | decreased |
| MIP-1beta | P13236 | CCL4 | # | 0.58 | decreased |
| MMP-2 | P08253 | MMP2 | ** | 0.57 | decreased |
| Prostate Specific Antigen, Free | P07288 | KLK3 | * | 0.4 | decreased |
| SGOT | P17174 | GOT1 | # | 5.98 | increased |
| Stem Cell Factor | P21583 | KITLG | # | 0.5 | decreased |
| Thrombopoietin | P40225 | THPO | # | 0.52 | decreased |
| Tissue Factor | P13726 | F3 | # | 0.35 | decreased |
| VCAM1 | P19320 | VCAM1 | # | 0.82 | decreased |
| VEGF | P15692 | VEGFA | # | 0.46 | decreased |

*, $p < 0.05$,
** $p < 0.01$,
$p < 0.001$ paired t-test

TABLE II

| Protein | gi accession | SwissProt | Symbol | P value | Drinking/Naïve | Level in Moderate or High Alcohol Consumer compared to non-drinker |
|---|---|---|---|---|---|---|
| alpha 1B glycoprotein precursor | 15778556 | P04217 | A1BG | * | 0.77 | decreased |
| Chain A, the structure of pentameric human serum amyloid P component | 576259 | P02743 | APCS1 | * | 1.5 | increased |
| clusterin | 55846712 | Q5ISQ2 | CLU | * | 0.38 | decreased |
| complement 9 | 2258128 | P02748 | C9 | * | 0.68 | decreased |
| complement C4A | 443671 | P0C0L4 | C4a | * | 0.64 | decreased |
| complement component 3 precursor | 115298678 | A7E236 | C3 | * | 2.38 | increased |
| fibronectin 1 isoform 6 preprotein | 47132549 | Q9UQS6 | FN1 | * | 1.75 | increased |
| histidine rich glycoprotein precursor | 4504489 | B9EK35 | HRG | * | 2.05 | increased |
| interalpha inhibitor 4 | 109039135 | | ITIH4 | * | 3.57 | increased |
| PEDF | 1144299 | P36955 | SERPIN F1 | * | 0.56 | decreased |
| retinol binding protein 4 | 55743122 | P02753 | RBP4 | * | 2.73 | increased |
| serum amyloid A4 | 109107113 | | SAA4 | | 4.18 | increased |

*, $p < 0.05$ paired t-test

TABLE III

| Protein Name | Protein Symbol | Bonferroni Corrected ANOVA | Naive vs Induction | Naive vs Drinking | Induction vs. Drinking | Final Biomarker Panel |
|---|---|---|---|---|---|---|
| Acid Phosphatase, Prostate | ACCP | ND | | | | |
| Adiponectin | ADIPOQ | p < 0.001 | NC | Decreased | Decreased | X |
| Alpha 1 Antitrypsin | Serpinela | NC | | | | |
| Alpha 2 Macroglobin | A2M | p < 0.001 | NC | Decreased | Decreased | X |
| Alpha-Fetoprotien | AFP | NC | | | | |
| Amyloid P Component Serum | APCS | p < 0.001 | Variable | NC | Variable | |
| ApoAI | APOA1 | p < 0.001 | NC | Variable | Variable | |
| ApoCIII | APOC3 | p < 0.001 | NC | Variable | Variable | |
| ApoH | APOH | NC | | | | |
| Beta 2 Mircoglobin | B2M | p < 0.001 | Variable | NC | Variable | |
| Brain-Derived Neurotrophic Factor | BDNF | NC | | | | |
| C Reactive Protein | CRP | NC | | | | |
| Calcitonin | CALCA | p < 0.001 | Variable | Decreased | Variable | |
| Carcinoembryonic Antigen-Related Cell Adhesion Molecule 5 | CEACAM5 | ND | | | | |
| CD 40 | CD40 | p < 0.001 | Decreased | Decreased | NC | X |
| CD 40 Ligand | CD40LG | p < 0.001 | Variable | Variable | NC | |
| Chemokine (C motif) Ligand 1 | XCL1 | ND | | | | |
| Chemokine (C—C motif) Ligand 11 | Ccl11 | p < 0.001 | Variable | Variable | NC | |
| Chemokine (C—C motif) Ligand 2 | CCL2 | NC | | | | |
| Chemokine (C—C motif) Ligand 22 | CCL22 | NC | | | | |
| Chemokine (C—C motif) Ligand 3 | CCL3 | p < 0.001 | Decreased | Decreased | NC | X |
| Chemokine (C—C motif) Ligand 4 | CCL4 | p < 0.001 | Decreased | Decreased | NC | X |
| Chemokine (C—C motif) Ligand 5 | CCL5 | NC | | | | |
| Chemokine (C—X—C motif) Ligand 5 | CXCL5 | p < 0.001 | Decreased | Decreased | NC | X |
| Colony Stimulating Factor 2 | CSF2 | p < 0.001 | Variable | NC | Variable | |
| Colony Stimulating Factor 3 | CSF3 | ND | | | | |
| Complement 3 | C3 | p < 0.001 | NC | Decreased | Decreased | X |
| Creatine Kinase, Muscle | CKM | ND | | | | |
| Endothelin-I | EDN1 | ND | | | | |
| Epidermal Growth Factor | EGF | p < 0.001 | Variable | Variable | NC | |
| Erythropoietin | EPO | ND | | | | |
| Factor III | F3 | p < 0.001 | Variable | Decreased | NC | |
| Factor VII | F7 | p < 0.001 | Decreased | Decreased | NC | X |
| Fatty Acid Binding Protein 3 | FABP3 | p < 0.001 | Variable | Decreased | NC | |
| Ferritin | FT | NC | | | | |
| Fibrinogen | FG | p < 0.001 | Variable | Variable | NC | |
| Fibroblast Growth Factor 2 | FGF2 | ND | | | | |
| Glutamic-Oxaloacetic Transaminase 1 | GOT1 | p < 0.001 | Increased | Increased | NC | X |
| Glutathione S-Transferase | GST | ND | | | | |
| Growth Hormone | GH1 | NC | | | | |
| Haptoglobin | HP | NC | | | | |
| IFN-gamma | IFNG | ND | | | | |
| IgA | IgA | NC | | | | |
| IgE | IgE | p < 0.001 | Decreased | Decreased | NC | X |
| IgM | IgM | NC | | | | |
| Insulin | INS | p < 0.001 | Variable | Variable | NC | |
| Insulin-Like Growth Factor 1 | IGF1 | p < 0.001 | Decreased | Decreased | NC | X |
| Intercelluar Adhesion Molecule 1 | ICAM1 | ND | | | | |
| Interleukin 1 Receptor Antagonist | IL1RN | NC | | | | |
| Interleukin 10 | IL10 | p < 0.001 | Variable | NC | Variable | |
| Interleukin 12 Subunit p40 | IL12-p40 | ND | | | | |
| Interleukin 12 Subunit p70 | IL12-p70 | p < 0.001 | Variable | Decreased | Variable | |
| Interleukin 13 | IL-13 | p < 0.001 | Variable | NC | Variable | |
| Interleukin 15 | IL-15 | NC | | | | |
| Interleukin 16 | IL-16 | ND | | | | |
| Interleukin 18 | IL-18 | p < 0.001 | Variable | Decreased | NC | |
| Interleukin 1alpha | IL-1alpha | ND | | | | |
| Interleukin 1beta | IL-1beta | ND | | | | |
| Interleukin 2 | IL-2 | p < 0.001 | Decreased | Decreased | NC | X |
| Interleukin 3 | IL-3 | ND | | | | |
| Interleukin 4 | IL-4 | ND | | | | |
| Interleukin 5 | IL5 | NC | | | | |
| Interleukin 6 | IL-6 | ND | | | | |
| Interleukin 7 | IL7 | p < 0.001 | Increased | Increased | NC | X |
| Interleukin 8 | IL8 | NC | | | | |
| Kallikrein-Related Peptidase 3 | KLK3 | p < 0.001 | Decreased | Decreased | NC | X |
| KIT Ligand | KITLG | p < 0.001 | Variable | Decreased | NC | |
| Leptin | LSL | ND | | | | |
| Lipoprotein (a) | LPA | ND | | | | |
| Lymphotoxin Alpha | LTA | NC | | | | |
| Matrix Metalloproteinase 2 | MMP2 | p < 0.001 | Decreased | Decreased | NC | X |
| Matrix Metalloproteinase 3 | MMP3 | ND | | | | |
| Matrix Metalloproteinase 9 | MMP9 | p < 0.001 | NC | Variable | NC | |
| Myeloperoxidase | MPO | NC | | | | |

TABLE III-continued

| Protein Name | Protein Symbol | Bonferroni Corrected ANOVA | Naive vs Induction | Naive vs Drinking | Induction vs. Drinking | Final Biomarker Panel |
|---|---|---|---|---|---|---|
| Myoglobin | MB | NC | | | | |
| Neighbor of BRCA1 Gene 1 | NBR1 | ND | | | | |
| NMDA receptor regulated 1 | NARG1 | ND | | | | |
| Pregnancy-Associated Plasma protein A, Pappalysin 1 | PAPPA | ND | | | | |
| S100 Calcium binding protein A12 | S100A12 | ND | | | | |
| Serine (or cysteine) Peptidase Inhibitor, Clade E, Member 1 | Serpine1 | p < 0.001 | Variable | NC | Increased | |
| Serpin Peptidase Inhibitor, Clade A (alpha-1 antiproteinase, antitrypsin), Member 7 | Serpina7 | ND | | | | |
| Sex Hormone-Binding Globulin | SHBG | p < 0.001 | Variable | Variable | NC | |
| Thrombopoietin | THPO | p < 0.001 | Decreased | Decreased | NC | X |
| Thyroid Stimulation Hormone | TSH | ND | | | | |
| Tissue Inhibitor of Matrix Meralloproteinase-1 | TIMP1 | p < 0.001 | Variable | Decreased | NC | |
| Tumor Necrosis Factor Alpha | TNFA | ND | | | | |
| Tumor Necrosis Factor Receptor Superfamily, Member 1B | TNFRSF1B | NC | | | | |
| Vascular Cell Adhesion Molecule 1 | VCAM1 | NC | | | | |
| Vascular Endothelial Growth Factor A | VEGFA | p < 0.001 | Decreased | Decreased | NC | X |
| von Willebrand Factor | VWF | ND | | | | |

TABLE IV

| Symbol | | Entrez Gene Name | Blood | Peripheral Immune Cells | Brain | Adipose | Bladder | Epidermis | Heart | Kidney | Large Intestine | Liver | Lung | Mammary Gland | Ovary |
|---|---|---|---|---|---|---|---|---|---|---|---|---|---|---|---|
| A2M | | alpha-2-macroglobulin | X | X | | | | | X | X | | X | X | | X |
| ADIPOQ | | adiponectin | X | X | X | X | X | X | X | X | X | | X | X | X |
| C3 | | complement component 3 | X | X | X | X | X | X | X | | X | X | X | X | X |
| CCL3 | MIP-1alpha | chemokine (C—C motif) ligand 3 | X | X | X | | | | | | | | | | |
| CCL4 | MIP-1beta | chemokine (C—C motif) ligand 4 | X | X | | | | | | X | | X | | | |
| CD40 | | CD40 molecule, TNF receptor family member 5 | X | X | X | X | X | | | X | X | X | X | X | X |
| CXCL5 | ENA-78 | chemokine (C—X—C motif) ligand 5 | X | X | | | | | | | | | | | |
| F7 | Factor 7 | coagulation factor VII | X | X | | | | | | | | X | | | |
| GOT1 | SGOT | glutamic-exaloacetic transaminase 1 | X | X | X | X | X | X | X | X | X | X | X | X | X |
| IgE | | immunoglobulin E | X | X | | | | | | | | | | | |
| IGF1 | | insulin-like growth factor 1 | X | X | X | X | X | X | X | X | X | X | X | X | X |
| IL2 | | interleukin 2 | X | X | | | | | | | | | | | |
| IL7 | | interleukin 7 | X | X | | X | | | | | | | | | |
| KLK3 | PSA | kallikrein-related peptidase 3 | X | | | | | | | | | | | X | |

TABLE IV-continued

| Symbol | | Entrez Gene Name | | | | | | | | | | | | |
|---|---|---|---|---|---|---|---|---|---|---|---|---|---|---|
| MMP2 | | matrix metallo-peptidase 2 | X | X | | X | X | X | X | X | X | X | X | | X |
| THPO | | thrombo-poietin | X | X | X | | | | | | | X | | | |
| VEGFA | | vascular endothelial growth factor A | X | X | X | X | X | X | X | X | X | X | X | X |

| Symbol | | Entrez Gene Name | Pan-creas | Pla-centa | Pros-tate Gland | Re-tina | Sali-vary Gland | Skeletal Muscle | Small Instes-tine | Spleen | Stom-ach | Testis | Thy-mus | Uter-us |
|---|---|---|---|---|---|---|---|---|---|---|---|---|---|---|
| A2M | | alpha-2-macro-globulin | | X | | X | | | | | | | | X |
| ADIPOQ | | adiponectin | X | X | X | | X | X | X | X | | X | X | X |
| C3 | | complement component 3 | | X | X | X | X | X | | X | X | | X | X |
| CCL3 | MIP-1alpha | chemokine (C—C motif) ligand 3 | | | | | | | | | | | | X |
| CCL4 | MIP-1beta | chemokine (C—C motif) ligand 4 | | | | | | | | X | X | | | X |
| CD40 | | CD40 molecule, TNF receptor family member 5 | X | X | | X | | | X | X | X | X | X | X |
| CXCL5 | ENA-78 | chemokine (C—X—C motif) ligand 5 | | | | | | | | | | | | |
| F7 | Factor 7 | coagulation factor VII | | | | | | | | | | | | |
| GOT1 | SGOT | glutamic-oxaloacetic transa-minase 1 | X | X | X | X | X | X | X | | X | | X | X |
| IgE | | immuno-globulin E | | | | | | | | | | | | |
| IGF1 | | insulin-like growth factor 1 | X | X | X | X | X | X | X | X | X | X | X | X |
| IL2 | | interleukin 2 | X | | | | | | | X | | | | |
| IL7 | | interleukin 7 | | | | | | | | X | X | | X | |
| KLK3 | PSA | kallikrein-related peptidase 3 | | | X | | X | | | | | | | |
| MMP2 | | matrix metallo-peptidase 2 | X | X | | X | | | | | | | | X |
| THPO | | thrombo-poietin | | | | | | | | | | | | |
| VEGFA | | vascular endothelial growth factor A | X | X | X | X | X | X | X | X | X | X | X | X |

TABLE V

| Master No. | Name | paired t-test p-value | Drinking/Naïve ratio | gi number |
|---|---|---|---|---|
| 556 | serum amyloid A4 | 0.000 | 4.18 | 119588821 |
| 109 | Interalpha inhibitor 4 | 0.003 | 3.57 | 31542984 |
| 100 | Interalpha inhibitor 4 | 0.005 | 3.55 | 31542984 |
| 589 | Serum amyloid A4 | 0.000 | 3.54 | 119588821 |
| 94 | Interalpha inhibitor 4 | 0.011 | 3.40 | 31542984 |
| 845 | Kininogen 1 isoform 2 | 0.000 | 3.26 | 37748641 |
| 638 | retinol-binding protein 4; plasma | 0.000 | 2.73 | 55743122 |
| 442 | apolipoprotein E precursor; APOE | 0.001 | 2.41 | 52078329 |
| 195 | histidine-rich glycoprotein precursor | 0.010 | 2.05 | 4504489 |
| 632 | apolipoprotein E precursor; APOE | 0.001 | 1.99 | 52078329 |
| 10 | fibronectin 1 | 0.024 | 1.93 | 34364820 |
| 502 | retinol binding protein 4; plasma | 0.038 | 1.91 | 7770173 |
| 194 | histidine-rich glycoprotein precursor | 0.004 | 1.86 | 4504489 |
| 8 | fibronectin 1 | 0.003 | 1.86 | 34364820 |
| 9 | fibronectin 1 isoform 6 preproprotein | 0.017 | 1.81 | 47132549 |
| 11 | fibronectin 1 | 0.016 | 1.69 | 34364820 |
| 512 | retinol binding protein 4; plasma | 0.001 | 1.69 | 7770173 |
| 12 | fibronectin 1 isoform 6 preproprotein | 0.017 | 1.68 | 47132549 |
| 489 | Serum Amyloid P | 0.000 | 1.62 | 576259 |
| 836 | clusterin | 0.005 | 1.59 | 55846712 |
| 756 | clusterin | 0.005 | 1.58 | 55846712 |
| 718 | retinol binding protein 4; plasma | 0.002 | 1.52 | 7770173 |
| 582 | pre-serum amyloid P component | 0.000 | 1.48 | 337758 |
| 491 | Serum Amyloid P | 0.001 | 1.47 | 576259 |
| 492 | Serum Amyloid P | 0.000 | 1.47 | 4502133 |
| 583 | pre-serum amyloid P component | 0.000 | 1.47 | 337758 |
| 781 | Serum Amyloid P | 0.026 | 1.46 | 576259 |
| 584 | pre-serum amyloid P component | 0.002 | 1.42 | 337758 |
| 749 | histidine-rich glycoprotein precursor | 0.013 | 1.33 | 4504489 |
| 748 | histidine-rich glycoprotein precursor | 0.048 | 1.31 | 4504489 |
| 719 | retinol binding protein 4; plasma | 0.015 | 1.31 | 7770173 |
| 818 | Prothrombin precursor | 0.024 | 1.28 | 62511155 |
| 488 | Serum Amyloid P | 0.022 | 1.27 | 576259 |
| 623 | MASP1 protein | 0.033 | 1.24 | 24981014 |
| 630 | Antithrombin | 0.041 | 1.22 | 999513 |
| 231 | Serpin peptidase inhibitor; clade D | 0.042 | 1.21 | 23273330 |
| 295 | Antithrombin | 0.047 | 1.18 | 999513 |
| 143 | Complement component C7 precursor | 0.035 | 1.15 | 75041872 |
| 741 | complement 9 | 0.016 | −1.47 | 2258128 |
| 785 | complement component C4A | 0.026 | −1.56 | 443671 |
| 312 | pigment epithelium-derived factor | 0.011 | −1.79 | 1144299 |
| 374 | ACTB protein | 0.001 | −1.88 | 15277503 |
| 311 | Antithrombin | 0.026 | −1.93 | 999513 |
| 721 | clusterin | 0.000 | −2.63 | 55846712 |
| 359 | Interalpha inhibitor 4 | 0.001 | −5.87 | 31542984 |
| 534 | Interalpha inhibitor 4 | 0.000 | −11.57 | 31542984 |

Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

We claim:

1. A method of differentiating non-ethanol consumption behavior from at least moderate ethanol consumption behavior by a human subject in the period of 2-4 weeks prior to collection of a subject plasma, blood or serum sample to be assayed, comprising:

assaying the subject plasma, blood or serum sample for a combination of two or more protein biomarkers selected from the group consisting of: A1BG, A2M, ADIPQ, APCS1, APOAI, C3, C4a, C9, CALCA, CCL3, CCL4, CD40, CLU, CSF2, CXCL5, EGF, F3, F7, FABP3, FN1, GOT1, HRG, IgE, IGF1, IL12p70, IL18, IL2, IL7, ITIH4, KITLG, KLK3, MMP2, RBP4, SAA4, SERPINF1, THPO, VCAM1 and VEGFA, to determine the level of the two or more protein biomarkers in the subject sample; and a) assaying a plurality of samples obtained from a population of individuals of the same gender as the subject who have not consumed ethanol in the period of 2-4 weeks prior to the collection of the plurality of samples for the two or more protein biomarkers to determine the level of the two or more protein biomarkers in the plurality of samples, producing a population standard; and comparing the level of the two or more protein biomarkers in the subject sample to the population standard or b) assaying a standard sample obtained from the subject when the subject had not consumed ethanol in the period of 2-4 weeks prior to the collection of the standard sample for the two or more protein biomarkers to determine the level of the two or more protein biomarkers in the standard sample, producing a subject standard; and comparing the level of the two or more protein biomarkers in the subject sample to the subject standard, wherein a decrease of at least 5% in level of A1BG, A2M, ADIPQ, C3, C4a, C9, CALCA, CCL3, CCL4, CD40, CLU, CXCL5, EGF, F3, F7, FABP3, IgE, IGF1, IL2, IL12p70, IL18, KITLG, KLK3, MMP2, SERPINF1, THPO, VEGFA or VCAM1 and/or an increase of at least 5% in levels of APCS1, APOAI, CSF2, FN1, GOT1, HRG, IL7, ITIH4, RBP4 or SAA4 in the subject sample compared to the population standard or subject standard indicates at least moderate ethanol consumption behavior by the subject in the 2-4 weeks prior to subject sample collection; and wherein a change of less than 5% in ADIPQ, A2M or C3 is indicative of moderate alcohol consumption behavior or less than moderate alcohol consumption behavior; and wherein a change of less than 5% in the level of two or more of A1BG, APCS1, APOAI, C4a, C9, CALCA, CCL3, CCL4, CD40, CLU, CSF2, CXCL5, EGF, F3, F7, FABP3, FN1, GOT1, HRG, IgE, IGF1, IL12p70, IL18, IL2, IL7, ITIH4, KITLG, KLK3, MMP2, RBP4, SAA4, SERPINF1, THPO, VCAM1 or VEGFA is indicative of non-ethanol consumption behavior by the subject in the 2-4 weeks prior to subject sample collection, thereby differentiating non-ethanol consumption behavior from at least moderate drinking behavior which is consumption of at least an average of 0.6 ounces of ethanol/day where the subject is female and at least an average of 1.2 ounces of ethanol/day where the subject is male.

2. The method of claim 1 wherein three biomarkers are assayed in the subject sample.

3. The method of claim 1 wherein four biomarkers are assayed in the subject sample.

4. The method of claim 1 wherein 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 or 38 biomarkers selected from the group consisting of: A1BG, A2M, ADIPQ, APCS1, APOAI, C3, C4a, C9, CALCA, CCL3, CCL4, CD40, CLU, CSF2, CXCL5, EGF, F3, F7, FABP3, FN1, GOT1, HRG, IgE, IGF1, IL12p70, IL18, IL2, IL7, ITIH4, KITLG, KLK3, MMP2, RBP4, SAA4, SERPINF1, THPO, VCAM1 and VEGFA, are assayed in the subject sample.

5. The method of claim 1 wherein the biomarkers are assayed by immunoassay.

6. The method of claim 1 wherein the biomarkers are assayed by a combination of gel electrophoresis and mass spectrometry.

7. The method of claim 1 wherein the biomarkers are assayed by liquid chromatography, mass spectrometry or a combination of liquid chromatography and mass spectrometry.

8. A method of differentiating between non-ethanol consumption behavior, moderate ethanol consumption behavior and heavy ethanol consumption behavior by a human subject in the period of 2-4 weeks prior to collection of a subject plasma, blood or serum sample to be assayed, comprising:
assaying the subject plasma, blood or serum sample for a combination of two or more protein biomarkers of ethanol non-consumption, moderate consumption or high consumption wherein at least one of the biomarkers is selected from the group consisting of: ADIPQ, A2M, and C3 and at least one of the biomarkers is selected from the group consisting of: CD40, CXCL5, F7, IgE, IGF1, IL2, IL7, CCL3, CCL4, MMP2, KLK3, GOT1, THPO and VEGFA, to determine the level of the two or more protein biomarkers in the subject sample; and
a) assaying a plurality of samples obtained from a population of individuals of the same gender as the subject who have not consumed ethanol in the period of 2-4 weeks prior to the collection of the plurality of samples for the two or more protein biomarkers to determine the level of the two or more protein biomarkers in the plurality of samples, producing a population standard; and comparing the level of the two or more protein biomarkers in the subject sample to the population standard,
or
b) assaying a standard sample obtained from the subject when the subject had not consumed ethanol in the period of 2-4 weeks prior to the collection of the standard sample for the two or more protein biomarkers to determine the level of the two or more protein biomarkers in the standard sample, producing a subject standard; and
wherein a decrease of at least 5% in the level of ADIPQ, A2M or C3 in the subject sample compared to the standard indicates heavy ethanol consumption behavior by the subject in the 2-4 weeks prior to subject sample collection; and wherein a decrease of at least 5% in level of CCL3, CCL4, CD40, CXCL5, F7, IgE, IGF1, IL2, KLK3, MMP2, THPO or VEGFA and an increase of at least 5% in levels of GOT1 and IL7 in the subject sample compared to the population standard or subject standard indicates at least moderate ethanol consumption behavior by the subject in the 2-4 weeks prior to subject sample collection; and wherein a change of less than 5% in ADIPQ, A2M or C3 is indicative of moderate alcohol consumption behavior or less than moderate alcohol consumption behavior; and wherein a change of less than 5% in the level of two or more of CCL3, CCL4, CD40, CXCL5, F7, GOT1, IgE, IGF1, IL2, IL7, KLK3, MMP2, THPO, or VEGFA is indicative of non-ethanol consumption behavior by the subject in the 2-4 weeks prior to subject sample collection, thereby differentiating non-drinking behavior, at least moderate drinking behavior which is consumption of at least an average of 0.6 ounces of ethanol/day where the subject is female and at least an average of 1.2 ounces of ethanol/day where the subject is male and heavy drinking behavior which is consumption of an average of more than 0.6 ounces of ethanol/day where the subject is female and an average of more than 1.2 ounces of ethanol/day where the subject is male.

9. A method of differentiating non-ethanol consumption behavior from at least moderate ethanol consumption behavior by a human subject in the period of 2-4 weeks prior to collection of a subject plasma, blood or serum sample to be assayed, comprising:
assaying the subject plasma, blood or serum sample for at least two protein biomarkers selected from the group consisting of: CD40, CXCL5, F7, IgE, IGF1, IL2, IL7, CCL3, CCL4, MMP2, KLK3, GOT1, THPO and VEGFA, to determine the level of the two or more protein biomarkers in the subject sample; and
a) assaying a plurality of samples obtained from a population of individuals of the same gender as the subject who have not consumed ethanol in the period of 2-4 weeks prior to the collection of the plurality of samples for the two or more protein biomarkers to determine the level of the two or more protein biomarkers in the plurality of samples, producing a population standard; and comparing the level of the two or more protein biomarkers in the subject sample to the population standard,
or
b) assaying a standard sample obtained from the subject when the subject had not consumed ethanol in the period of 2-4 weeks prior to the collection of the standard sample for the two or more protein biomarkers to determine the level of the two or more protein biomarkers in the standard sample, producing a subject standard; and comparing the level of the two or more protein biomarkers in the subject sample to the subject standard, wherein a decrease of at least 5% in level of CCL3, CCL4, CD40, CXCL5, F7, IgE, IGF1, IL2, KLK3, MMP2, THPO, or VEGFA and/or an increase of at least 5% in levels of GOT1 or IL7 in the subject sample compared to the population standard or subject standard indicates at least moderate ethanol consumption behavior by the subject in the 2-4 weeks prior to subject sample collection; and wherein a change of less than 5% in the level of two or more of CD40, CXCL5, F7, IgE, IGF1, IL2, IL7, CCL3, CCL4, MMP2, KLK3, GOT1, THPO or VEGFA is indicative of non-ethanol consumption behavior by the subject in the 2-4 weeks prior to subject sample collection, thereby differentiating non-ethanol consumption behavior from at least moderate drinking behavior which is consumption of at least an average of 0.6 ounces of ethanol/day where the subject is female and at least an average of 1.2 ounces of ethanol/day where the subject is male.

10. The method of claim 9 comprising: assaying a subject sample for: CD40, CXCL5, F7, IgE, IGF1, IL2, IL7, CCL3, CCL4, MMP2, KLK3, GOT1, THPO and VEGFA.

11. A method of differentiating moderate ethanol consumption behavior from heavy ethanol consumption behavior by a human subject in the period of 2-4 weeks prior to collection of a subject plasma, blood or serum sample to be assayed, comprising:

assaying the subject plasma, blood or serum sample by a method comprising a binding assay or mass spectrometry, for at least two protein biomarkers selected from the group consisting of: ADIPQ, A2M and C3, to determine the level of the at least two biomarkers in the subject sample; and a) assaying a plurality of samples obtained from a population of individuals of the same gender as the subject who have not consumed ethanol in the period of 2-4 weeks prior to the collection of the plurality of samples for the two or more protein biomarkers to determine the level of the two or more protein biomarkers in the plurality of samples, producing a population standard; and comparing the level of the two or more protein biomarkers in the subject sample to the population standard, or b) assaying a standard sample obtained from the subject when the subject had not consumed ethanol in the period of 2-4 weeks prior to the collection of the standard sample for the two or more protein biomarkers to determine the level of the two or more protein biomarkers in the standard sample, producing a subject standard; and wherein a decrease of at least 5% in the level of at least two of ADIPQ, A2M or C3 in the subject sample compared to the population standard or subject standard indicates heavy ethanol consumption behavior by the subject in the 2-4 weeks prior to subject sample collection; and wherein a change of less than 5% in the level of at least two of ADIPQ, A2M or C3 is indicative of moderate ethanol consumption behavior or less than moderate alcohol consumption behavior by the subject in the 2-4 weeks prior to subject sample collection, thereby differentiating moderate ethanol consumption which is consumption of at least an average of 0.6 ounces of ethanol/day where the subject is female and at least an average of 1.2 ounces of ethanol/day where the subject is male from heavy ethanol consumption which is consumption of an average of more than 0.6 ounces of ethanol/day where the subject is female and an average of more than 1.2 ounces of ethanol/day where the subject is male, in the subject.

12. The method of claim 11 comprising assaying a subject sample for ADIPQ, A2M and C3, to determine the level of ADIPQ, A2M and C3 biomarkers in the sample; and comparing the level of ADIPQ, A2M and C3 in the sample to the population standard or subject standard, thereby differentiating moderate ethanol consumption behavior or less than moderate alcohol consumption behavior from heavy ethanol consumption behavior in the subject.

* * * * *